United States Patent [19]
Crothall

[11] Patent Number: 6,049,727
[45] Date of Patent: Apr. 11, 2000

[54] IMPLANTABLE SENSOR AND SYSTEM FOR IN VIVO MEASUREMENT AND CONTROL OF FLUID CONSTITUENT LEVELS

[75] Inventor: Katherine D. Crothall, Haverford, Pa.

[73] Assignee: Animas Corporation, Malvern, Pa.

[21] Appl. No.: 09/054,806

[22] Filed: Apr. 3, 1998

Related U.S. Application Data

[63] Continuation of application No. PCT/US97/11832, Jul. 8, 1997, which is a continuation-in-part of application No. PCT/US96/11435, Jul. 8, 1996.

[51] Int. Cl.$^7$ .................................................... A61K 9/22
[52] U.S. Cl. ........................ 600/310; 600/316; 600/322; 604/891.1
[58] Field of Search .................................. 600/310, 316, 600/322, 326, 473, 476; 604/50, 66, 67, 890.1, 891.1; 356/39

[56] References Cited

U.S. PATENT DOCUMENTS

| | | |
|---|---|---|
| 3,837,339 | 9/1974 | Aisenbert et al. . |
| 4,013,074 | 3/1977 | Siposs . |
| 4,073,292 | 2/1978 | Edelman . |
| 4,398,908 | 8/1983 | Siposs . |
| 4,435,173 | 3/1984 | Siposs et al. . |
| 4,538,616 | 9/1985 | Rogoff . |
| 4,621,643 | 11/1986 | New, Jr. et al. . |
| 4,633,878 | 1/1987 | Bombardieri . |
| 4,679,562 | 7/1987 | Luksha . |
| 4,704,029 | 11/1987 | Van Heuvelen . |
| 4,807,629 | 2/1989 | Baudino et al. . |
| 4,822,336 | 4/1989 | DiTraglia . |
| 4,825,879 | 5/1989 | Tan et al. . |
| 4,830,488 | 5/1989 | Heinze et al. . |
| 4,865,038 | 9/1989 | Rich et al. . |
| 4,890,621 | 1/1990 | Hakky . |
| 4,979,509 | 12/1990 | Hakky . |
| 4,996,419 | 2/1991 | Morey . |
| 5,054,487 | 10/1991 | Clarke . |

(List continued on next page.)

FOREIGN PATENT DOCUMENTS

| | | |
|---|---|---|
| 4-15046 | 1/1992 | Japan . |
| 92/11801 | 7/1992 | WIPO . |

OTHER PUBLICATIONS

Rebrin, A., et al., Automated Feedback Control of Subcutaneous Glucose Concentraction in Diabetic Dogs, *Diabetologia*, vol. 32, pp. 573–576, 1989.

Koudelka, M., et al., In–Vivo Behaviour of Hypodermically Implanted Microfabricated Glucose Sensors, *Biosensors & Bioelectronics*, vol. 6, pp. 31–36, 1991.

Fischer et al., "Assessment of subcutaneous glucose concentration: validation of the wick technique as a reference for implanted electrochemcial sensors in normal and diabetic dogs", Diabetologia, vol. 30, pp. 940–945. Date 1987.

(List continued on next page.)

*Primary Examiner*—Eric F. Winakur
*Attorney, Agent, or Firm*—Akin, Gump, Strauss, Hauer & Feld, L.L.P.

[57] ABSTRACT

An in vivo implantable sensor obtains spectra of body fluid constituents and processes the spectra to determine the concentration of a constituent of the body fluid. The sensor includes an optical source and detector. The source emits light at a 'plurality of different, discrete wavelengths, including at least one wavelength in the infrared region. The light interacts with the body fluid and is received at the detector. The light at the plurality of different wavelengths has a substantially collinear optical path through the fluid with respect to each other. When measuring fluid constituents in a blood vessel, such as blood glucose, the light at the plurality of different wavelengths is emitted in a substantially single period of time. The spectra is corrected for artifacts introduced from extraneous tissue in the optical path between the source and the detector. The sensor is fully implanted and is set in place to allow plural measurements to be taken at different time periods from a single in vivo position. The light source emits at at least three different wavelengths.

67 Claims, 7 Drawing Sheets

U.S. PATENT DOCUMENTS

| | | |
|---|---|---|
| 5,101,814 | 4/1992 | Palti . |
| 5,127,406 | 7/1992 | Yamaguchi . |
| 5,179,951 | 1/1993 | Knudson . |
| 5,190,041 | 3/1993 | Palti . |
| 5,204,532 | 4/1993 | Rosenthal . |
| 5,305,745 | 4/1994 | Zacouto . |
| 5,353,792 | 10/1994 | Lubbers et al. . |
| 5,361,759 | 11/1994 | Genevier et al. . |
| 5,368,028 | 11/1994 | Palti . |
| 5,428,635 | 6/1995 | Zhiglinsky et al. . |
| 5,457,760 | 10/1995 | Mizrahi . |
| 5,474,552 | 12/1995 | Palti . |
| 5,574,807 | 11/1996 | Snitzer . |
| 5,589,684 | 12/1996 | Ventrudo et al. . |
| 5,598,841 | 2/1997 | Taniji et al. . |
| 5,608,825 | 3/1997 | Ip . |
| 5,627,848 | 5/1997 | Fermann et al. . |

OTHER PUBLICATIONS

Pickup, J.C. et al., "In vivo molecular sensing in diabetes mellitus: an implantable glucose sensor with direct electron transfer", Diabetologia, vol. 32, pp. 213–217. Date 1989.

Zeller, H., et al., "Blood glucose measurement by infrared spectroscopy", International Journal of Artificial Organs, vol. 12, p. 129 (1989).

Arnold, M.A., et al., Determination of physiological levels of glucose in an aqueous matrix with digitally filtered Fourier Transformation Neat–Infrared Spectra, Analytical Chemistry, vol. 62, pp. 1457–1464 (1990).

Shichiri, M., et al., An artificial endocrine pancreas—problems awaiting solution for long term clinical applications of a glucose sensor, Frontiers of Medical and Biologial Engineering, vol. 3, 283 (1991).

Heise, H.M., et al., Noninvasive blood glucose sensors based on near–infrared spectroscopy, Artificial Organs, vol. 18, 439 (1994).

Heise, H.M., et al., Multivariate Determination of Glucose in Whole Blood by Attenuated Total Reflection Infrared Spectroscopy, Analytical Chemistry, vol. 61 No. 18, Sep. 15, 1989.

Johnson, K.W., et al., In Vivo Evaluation of an Electroenzymatic Glucose Sensor Implanted in Subcutaneous Tissue, Biosensors & Bioelectronics, vol. 7, pp. 709–714, 1992.

Miyazawa, T., Characteristic Infrared Bands of Monosubstituted Amides, The Journal of Chemical Physics, vol. 24, No. 2, Feb. 1956.

Abe, T., et al., Characterization of Glucose Microsensors for Intracellular Measurements, Anal. Chem. 1992, vol. 64, pp. 2160–2163, 1992.

Conway, J., Ph.D., A New Approach for the Estimation of Body Composition: Infrared Interactance, The American Journal of Clinical Nutrition 40: Dec., 1984, pp. 1123–1130.

Abel, P., et al., The $GOD-H_2O_2$–Electrode as an Approach to Implantable Glucose Sensors. (no date available).

Lanza, E., Determination of Moisture, Protein, Fat, and Calories in Raw Pork and Beef by Near Infrared Spectroscopy.

Tallagrand, T., et al., Evaluation of Implantable Glucose Enzyme–Based Sensors with Extracorporeal Blood Shunt, 1988. (best copy available).

Mathlouthi, M., Laser–Raman Spectra of D–Glucose and Sucrose in Aqueous Solution, Carbohydrate Research, vol. 81, (1980) pp. 203–212.

Gough, D.A., Issues Related to In Vitro Operation of Potentially Implantable Enzyme Electrode Glucose Sensors. (no date available).

Stewart, R., et al., Infrared Analysis of Serum Protein from One Hundred and Five Hundred Adults, J. Lab. & Clin. Med. Sep. 1960, vol. 56, No. 3.

Clark, L.C., et al., Long–Term Stability of Electroenzymatic Glucose Sensors Implanted in Mice, Trans Am Soc Artif Intern Organs, vol. 34, 1988.

Ertefai, S., et al., Physiological Preparation for Studying the Response of Subcutaneously Implanted Glucose and Oxygen Sensors, Biomed Engineering, vol. 11, Sep. 1989.

Marbach, R., et al., On the Efficiency of Algorithms for Multivariate Linear Calibration used in Analytical Spectroscopy, Trends in Analytical Chemistry, vol. 11, No. 8, 1992.

Chang, K., et al., Validation and Bioengineering Aspects of an Implantable Glucose Sensor. (no date available).

Heise, H.M., et al, Multivariate Detrmination of Blood Substrates in Human Plasma, International Conference on Fourier Transform Spectroscopy (1991).

Pickup, J.C., et al., Progress Towards In Vivo Glucose Sensing with a Ferrocene–Mediated Amperometric Enzyme Electrode. (no date available).

Bauer, B., et al., Monitoring of Glucose in Biological Fluids by Fourier–Transform Infrared Spectrometry with a Cylindrical Internal Reflectance Cell, Analytical Chimica Acta, (1987).

Guyton, J.R., et al., The Development of an Implantable electrochemical Glucose Sensor: Response to Glucose in Bovine Serum Ultrafiltrate. (no date available).

Haaland, D., et al., Reagentless Near–Infrared Determination of Glucose in Whole Blood Using Multivariate Calibration, Applied Spectroscopy, vol. 46, No. 10, 1992.

Cammann K. Implantable Electrochemical Glucose Sensors—State of the Art, (no date available).

Hopkinson, J., et al., Applications of Attenuated Total Reflection in the Infrared Analysis of Carbohydrates and Biological Whole Cell Samples in Aqueous Solution, Analyst, vol. 112, Apr. 1987.

Xie, S., Ph.D., et al., Performances of Potentially Implantable. Rechargeable Glucose Sensors In Vitro at Body Temperature, Biomedical Instrumentation & Technology, Sep./Oct. 1991 pp. 393–399.

Kaiser, N., Communication, Transaction on Biomedical Engineering, vol. BE–26, No. 10, Oct. 1979.

Wilson, G., et al., Progress toward the Development of an Implantable Sensor for Glucose, Clinical Chemistry, vol. 38, No. 9, 1992.

Guyton, A., M.D., Insulin, Glucagon, and Diabetes Mellitus, Textbook of Medical Physiology, 8th Edition.

Moatti–Sirat, D., et al., Towards Continous Glucose Monitoring In Vivo Evaluation of a Miniaturized Glucose Sensor Implanted for Several Days in Rat Subcutaneous Tissue, Diabetology, vol. 35, pp. 224–230, 1992.

Velho, G., et al., Strategies for Calibrating a Subcutaneous Glucose Sensor, Biomed. Biochimica Acta (1989).

Armour, J.C., et al., Application of Chronic Intravascular Blood Glucose Sensor in Dogs, Diabetes, Dec. 1990.

Velho, G., et al., Determination of Peritoneal Glucose Kinetics in Rats: Implications for the Peritoneal Implantation of Closed–Loop Insulin Delivery Systems, Diabetologia (1989) vol. 32, pp. 331–336.

von Woedtke, T., et al., Implantable Glucose Sensors: Comparison between In Vitro and In Vivo Kinetics, *The International Journal or Artificial Organs*, vol. 14, No. 8, pp. 473–481, 1991.

Kolendorf, K., et al., Determination of 24–Hour Insulin Infusion Pattern by an Artificial Endocrine Pancreas for Intravenous Insulin Infusion with a Miniature Pump, *Horm. Metab. Res.* vol. 13, pp. 245–249 (1981).

Poitout, V., et al., In Vitro and In Vivo Evaluation in Dogs of a Miniaturized Glucose Sensor. (no date available).

Goetz, F., Conference on Beta Cell Function, Transplantation, and Implantable Glucose Sensors: A Summary, *Metabolism*, vol. 23, No. 9, Sep., 1974.

Hollander, P.M.D., et al. Diabetes in pregnancy, *Park Nicollet Medical Center*.

Fischer, U. et al., A Membrane Combination for Implantable Glucose Sensors. Measurement in Undiluted Biological Fluids, *Trans Am Soc Artif Intern Organs*, vol. 28, 1982.

Robinson, R.M., et al., Noninvasive Glucose Monitoring in Diabetic Patients: A Preliminary Evaluation, *Clinical Chemistry*, vol. 38, No. 9, 1992.

Woedtke, et al., In Situ Calibration of Implanted Electrochemical Glucose Sensors, *Biomed Biochim Acta*, vol. 48, 1989.

Schultz, J.S., et al., Affinity Sensor: A New Technique for Developing Implantable Sensors for Glucose and Other Metabolites, *Diabetes Care*, vol. 5, No. 3, May–Jun. 1982.

Pickup, J.C., et al., Potentially–Implantable, Amperometric Glucose sensors with Medical Electron Transfer: Improving the Operating Stability, *Biosensors* (1989).

Clark, L.C., Long–Term Implantation of Voltammetric Oxidase/Peroxide Glucose Sensors in the Rat Peritoneum, *Methods in Enzymology*, vol. 137.

Drake, R.F., et al., In Vitro and In Vivo Testing of an Electrocatalytic Glucose Sensor, *Electrocatalytic Glucose Sensor*.

Fisher, et al., Experience with an Implantable Glucose Sensor as a Prerequisite of an Artificial Beta Cell, *Biomed Biochim Acta*, vol. 43, 1984.

Lerner, H., et al., Measurement of Glucose Concentration in the Presence of Coreactants with a Platinum Electrode, *Diabetes Care*, vol. 5, No. 3 May–Jun. 1982.

Kondo, et al., Trial of new Vessel Access Type Glucose Sensor for Implantable Artificial Pancreas In Vivo, *Trans Am Soc Artif Intern Organ*, vol. 27, 1981.

Gilligan, B., J. MS, DVM, et al., Evaluation of a Subcutaneous Glucose Sensor out to Three Months in a Dog Model, *Diabetes Care*, vol. 17, No. 8, Aug. 1994.

Velho, G. et al., In Vitro and In Vivo Stability of Electrode Potentials in Needle–Type Glucose Sensors, *Diabetes*, vol. 38, Feb. 1989.

Fischer, U., et al., Wick Technique: Reference Method for Implanted Glucose Sensors, *Artificial Organs*, vol. 13, No. 15, 1989.

Hashiguchi, Y., M.D., et al., Development of a Miniaturized Glucose Monitoring System by Combining a Needle–Type Glucose Sensor With Microdialysis Sampling Method, *Diabetes Care*, vol. 17, No. 5, May 1994.

Preidel, W., et al., In Vivo Experiment with the Electrocatyic Glucose Sensor in Sheep, *Biosensors & Bioelectronics*, vol. 8 pp. 299–306, 1993.

Moussy, F., et al., Performance of Subcutaneously Implanted Needle–Type Glucose Sensors Employing a Novel Trilayer Coating, *Analytical Chemistry*, vol. 65, pp. 2072–2077, 1993.

Shichiri, M., et al., In Vivo Characteristics of Needle–Type Glucose Sensor–Measurement of Subcutaneous Glucose Concentrations in Human Volunteers. (no date available).

Poitout, V. et al., A Glucose Monitoring System for on Line Estimation in Man of Blood Glucose Concentration Using a Miniaturized Glucose Sensor Implanted in the Subcutaneous Tissue and a Wearable Control Unit, *Diabetologia*, vol. 36, pp. 658–663, 1993.

Koudelka, M., et al., In Vivo Behavior of Hypodermically Implanted Microfabricated Glucose Sensors, *Biosensors & Bioelectronics*, vol. 6, pp. 31–36, 1991.

Sternberg, R., et al., Study and Development of Multilayer Needle–Type Enzyme based Glucose Microsensors, *Biosensors*, vol. 4, pp. 27–40, 1988.

Shichiri, M., et al., Wearable Artificial Endocrine Pancras with Needle–Type Glucose Sensor, *The Lancet*, Nov. 20, 1982.

Shaw, G.W., et al., In Vitro Testing of a Simply constructed, Highly Stabel Glucose Sensor Suitable for Implantation in diabetic Patients, *Biosensors & Bioelectronics*, vol. 6, pp. 401–406, 1991.

Clark, L.C. Jr., et al., Implanted Electroenzymatic Glucose Sensors, *Diabetes Care*, vol. 5, No. 3, May–Jun. 1982.

Pickup, J., et al., Implantable Glucose Sensors: Choosing the Appropriate Sensing Strategy, *Biosensors*, vol. 3, pp. 335–346, 1987.

Fischer, et al., Oxygen Tension at the Subcutaneous Implantation Site of Glucose Sensors, *Biochem. Bichim Acta*, vol. 48, pp. 965–971, 1989.

Kondo, T., et al., A Miniature Glucose Sensor, Implantable in the Blood Stream, *Diabetes Care*, vol. 5, No. 3, May–Jun. 1982.

Rebrin, K. et al., Subcutaneous Glucose Monitoring by Means of Elecrochemical Sensors: Fiction or Reality?. *Journal of Biomedical Engineering*, vol. 14, Jan. 1992.

McKean, B., et al., A Telemetry–Instrumentation System for Chronically Implanted Glucose and Oxygen Sensors, *IEEE Transactions of Biomedical Engineering*, vol. 35, No. 7, Jul. 1988.

Claremont, D.J., et al., Subcutaneous Implantation of a Ferrocene–Mediated glucose sensor in Pigs, *Diabetologia*, vol. 29, pp. 817–821, 1986.

C. Meyerhoff, et al., Use of the Microdialysis Technique in the Monitoring of Subcutaneous Tissue Glucose Concentration, *The International Journal of Artificial Organs*, vol. 16, No. 5, pp. 268–275, 1993.

Galactic Industries Corp. web pages, "About Galactic" and "PLSplusIQ", downloaded from Galactic website (www.galactic.com) on Jun. 19, 1995, 5 pages.

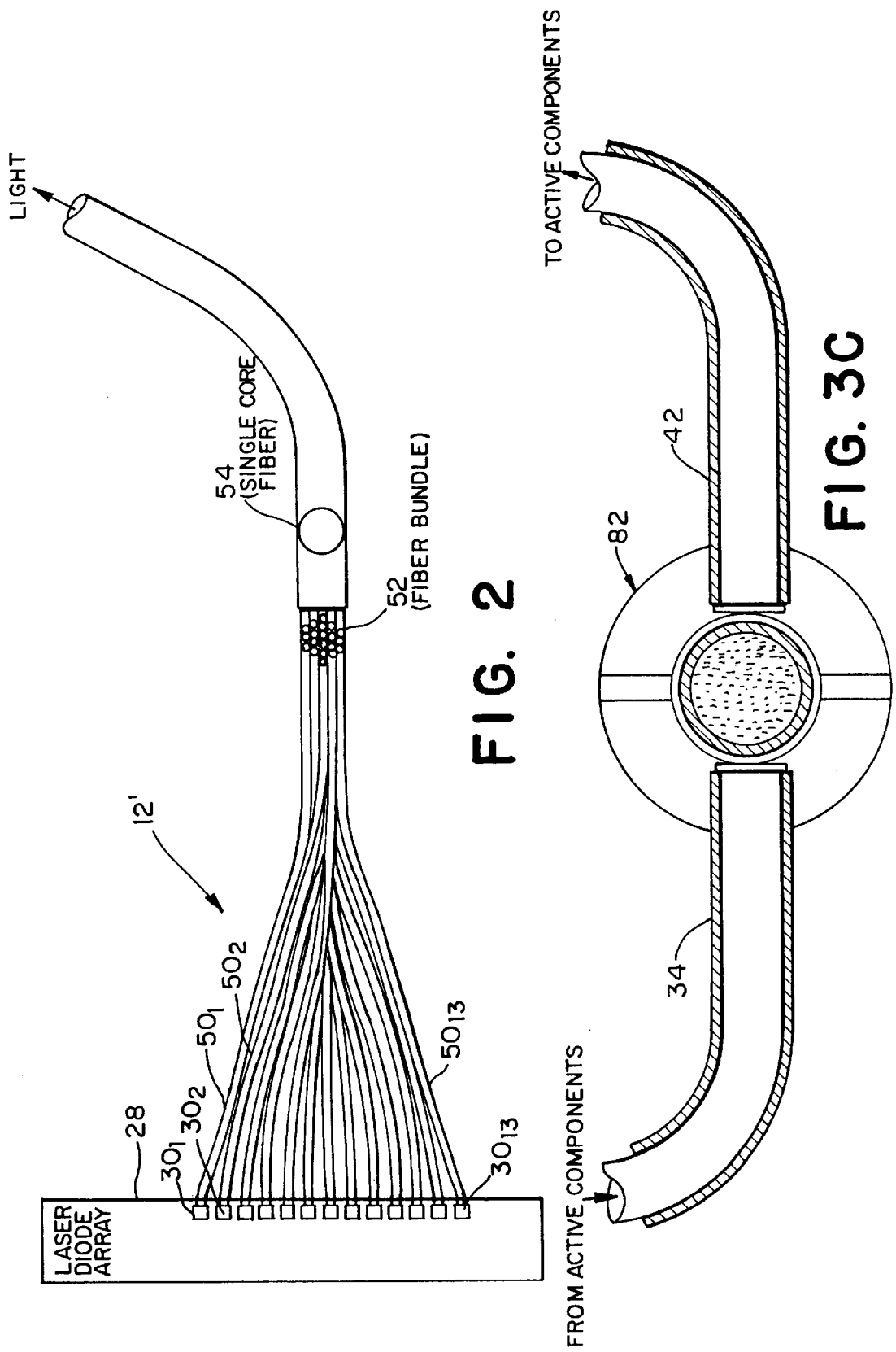

IMPLANTABLE SENSOR AND SYSTEM FOR IN VIVO MEASUREMENT AND CONTROL OF FLUID CONSTITUENT LEVELS

CROSS-REFERENCE TO RELATED APPLICATIONS

This application is a continuation of copending International Application No. PCT/US97/11832 filed Jul. 8, 1997, entitled "IMPLANTABLE SENSOR AND SYSTEM FOR IN VIVO MEASUREMENT AND CONTROL OF FLUID CONSTITUENT LEVELS" and which designated the United States, which, in turn, is a continuation-in-part of International Application No. PCT/US96/11435 filed Jul. 8, 1996, entitled "IMPLANTABLE SENSOR AND SYSTEM FOR MEASUREMENT AND CONTROL OF BLOOD CONSTITUENT LEVELS" and which designated the United States.

BACKGROUND OF THE INVENTION

The present invention relates generally to medical apparatus and methods for determining in vivo the concentration of a chemical constituent in a body fluid using direct spectroscopic analysis of the fluid, and for removing or obviating actual or potential artifacts from measured spectral data.

In medicine, the measurement of the composition of blood and other body fluids is an often invaluable diagnostic tool and is used as a basis for the titration of medicines and the determination of therapy. Broadly speaking, there are two classes of devices used for the measurement of chemical constituents; chemical and optical. The chemical techniques are the most wide-spread and essentially all techniques used in the clinical laboratory are based on chemical techniques. Chemical techniques invariably rely upon the constituent reacting with a "reagent" and either an optical or electrical measurement of the reagent or the by-products of the reaction. Unfortunately, the present chemical techniques have many drawbacks, including the following drawbacks:

(1) Present commercially available instruments are invasive and require, generally, a drop of fluid to determine the chemical constituents.

(2) Present commercial instruments require a unique chemical reagent for the determination of each constituent. The reagents are generally expendable and need to be replaced, frequently after each measurement. Instrument maintenance is thus expensive and inconvenient, particularly for an implantable device.

(3) Implantable chemical sensors suffer from drift due to lack of stability of the reagents at body temperature over a period of time, and short lifetime due to biocompatibility problems.

(4) Chemical sensors generally consume the constituent they are to measure, affecting accuracy. In an implantable sensor, tissue reaction with the sensor invariably diminishes the supply of the constituents, causing a reduction in accuracy.

Optical techniques have been hailed by researchers as a means to overcome all the problems associated with chemical techniques, as they do not utilize a reagent or require any sort of chemical reaction and they do not require direct interaction of the sensor with the chemical constituent. Optical techniques can theoretically provide continuous, non-invasive, simultaneous determination of multiple chemical constituents. Despite the promise of optical techniques and the efforts by numerous groups throughout the world to perfect such techniques, optical techniques are rarely used in clinical medicine. The pulse oximeter and an instrument which measures percent of body fat are notable exceptions.

One sensor particularly sought by researchers has been a home use glucose sensor for insulin-dependent diabetics. Ideally, such a sensor would be non-invasive or permanently implantable, would provide a continuous or quasi-continuous means of measurement of blood glucose, and would be accurate over the physiological range of blood chemistry and other conditions and would require minimal patient intervention. There are reportedly over 60 groups throughout the world who are currently attempting to develop such at sensor, yet no group is known to be close to success. The rationale behind these efforts are the staggering cost of the complication of diabetes on both the patient and the health care system. Studies have shown that the complications of diabetes can be reduced significantly with tight control of blood sugar.

Diabetes is a major chronic disease, costing the United States between $90 and $110 billion annually in health care costs alone. Approximately 750,000 people in United States have insulin dependent diabetes mellitus (IDDM), also known as Type I, Juvenile onset, or ketosis prone diabetes. Another 16 million people have non-insulin dependent diabetes mellitus (NIDDM), also known as Type II or adult onset diabetes. Globally, the World Health Organization estimates the number of diabetics to exceed 80 million, many of whom are undiagnosed.

Acute complications from diabetes involve metabolic abnormalities such as hypoglycemia and ketoacidosis. Long term complications involve the blood vessels and tissues leading to retinopathy, stroke, myocardial infarction, heart failure, arterial occlusive diseases, nephropathy, kidney failure, and peripheral neuropathy. For example, diabetes produced blindness in over 39,000 people within the United States last year. About 25% of people with IDDM and 10% of the people with NIDDM have proliferative retinopathy within 15 years after diagnosis of diabetes. About 34% of IDDM and 19% of NIDDM have diabetic kidney disease within 15 years of diagnosis. Although all these diseases occur in the general population, they occur early and far more frequently, and progress more rapidly in diabetics.

There have been several studies which have proven that the occurrence or progression of complications of diabetes can be reduced substantially in IDDM diabetics if their blood sugars can be maintained at near normal levels. The Diabetes Control and Complications Trial (DCCT) was a nine year randomized prospective study involving more than 1,400 subjects. The DCCT compared the complication rate following standard IDDM management (mean glucose 195 mg/dl) versus tight control with frequent fingerstick blood testing and frequent insulin injections (mean glucose levels 155 mg/dl). Intensive therapy was shown to reduce the risk for development of retinopathy by 76% and reduce the progression of retinopathy by 54%. A smaller scale study known as the Oslo study followed 45 insulin dependent diabetics, randomized into three groups: multiple insulin injections, continuous subcutaneous insulin infusion (CSII), and conventional twice daily insulin injections. Near normoglycemia was obtained with CSII and multiple injections, but not with conventional therapy. After two years, the CSII and multiple injections groups showed little deterioration as measured by the number of microaneurisms and hemorrhages whereas the conventional therapy group showed significant deterioration.

Several observations can be made regarding these studies:

Although tight control reduces the secondary complication rate of diabetes significantly compared to loosely controlled diabetes, the risk of these complications is still several times higher than with the non-diabetic population.

Tight control involves a significant amount of inconvenience and pain, rendering such compliance an elusive goal for many, if not most diabetics. For example, to determine the appropriate insulin injection, a diabetic must measure his blood glucose at least five to six times daily which involves pricking one's fingers to draw blood and then measuring for blood glucose with a glucometer. For many patients, the drawing of blood is painful and inconvenient, in fact substantially more painful and inconvenient than the insulin injection.

Both studies pointed to a significant (two to three times) increase in severe and at times symptomless hypoglycemia for patients under tight control versus those under conventional therapy. Severe hypoglycemia leads to loss of consciousness and at times even coma. In patients under tight control, the incidence of severe hypoglycemia ran 0.6 to 0.8 incidents per year whereas for patients under conventional therapy, the incidence ran 0.2 to 0.4 incidents per year. For this reason, a continuous or quasi-continuous sensor which can provide an alarm is desired.

The blood glucose levels with patients under a tight control regime has a mean value of 155 mg/dl and varies from a low of 120 mg/dl to a high of 190 mg/dl over the course of a day. These levels are still quite a bit higher than the glycemia of non-diabetics which have a mean glycemia of 110 mg/dl and a variance from 90 to 120 mg/dl over the course of a day. Although the DCCT indicates the desirability of even a further reduction of blood glucose, the risk of hypoglycemia mitigates against any further reduction.

It is believed that a system which can maintain blood sugars to true normal levels (90–120 mg/dl) could potentially eliminate the complications of diabetes. Such a system would have an insulin infusion pump and a glucose sensor. Neither pump nor sensor would require much interaction on the part of the patient and would certainly be painless. The pumps are already well developed. The missing link is a sensor which can continuously measure blood sugar, is either non-invasive or implantable, and is accurate over a large range of physiological ranges.

The approaches taken by researchers to measure blood glucose consist of a variety of techniques, both optical and chemical. A variety of researchers have attempted implantable chemical sensors, but these sensor seem to invariably fail for the reasons outlined above. U.S. Pat. No. 5,353,792 (Lubbers et al.) discloses a variation on the chemical sensor which uses "optically excitable and readable indicating substances", one of which could presumably interact with glucose. The drawback to this approach is the same as other chemical techniques, namely the substances need to presumably interact directly with the constituent to be measured and therefore can potentially be depleted with time, or alternatively, the substances become blocked from interaction with the constituent due to encapsulation tissue. Another variation to the Lubbers et al. approach are affinity sensors based on fiber optics, described in Schultz, J. S. et al., "Affinity Sensor: A New Technique for Developing Implantable Sensors for Glucose and Other Metabolites," Diabetes Care, Vol. 5, No. 3, pp. 243, May–June 1982; and Mansouri, S. et al., Bio/technology, Vol. 2, pp. 385, 1984. These sensors also suffer from long term reduction in sensitivity.

The optical techniques also include a variety of approaches. Most of the approaches attempted have been non-invasive, transcutaneous means utilizing infrared spectroscopy. Infrared spectroscopy is based on the absorption of infrared light. The amount of absorption is dependent upon the concentration and light pathlength through the fluid being measured. Each chemical constituent has its own unique absorption spectra, depending upon the weight of each atom and strength of each molecular bond in a molecule. In theory, given enough signal to noise, one should be able to determine precisely the presence and concentration of each chemical constituent in a fluid, such as blood. Transcutaneous infrared spectroscopic techniques suffer from variability in optical coupling, poor signal to noise, and excessive artifacts. No device utilizing such techniques has yet been shown to work reliably. One technique disclosed in U.S. patent application Ser. No. 08/500,388, filed Jul. 6, 1995, entitled "IMPLANTABLE SENSOR AND SYSTEM FOR MEASUREMENT AND CONTROL OF BLOOD CONSTITUENT LEVELS," partially solved the coupling and signal to noise problem by implanting the sensor, as opposed to using it transcutaneously. A more detailed analysis of these two approaches is discussed below.

Several other optical approaches have also been attempted. U.S. Pat. No. 4,704,029 (Van Heuvelen) discloses an implantable device in which the concentration of glucose is inferred by a measurement of the refractive index of blood by an optical device in direct contact with blood. This device has many drawbacks, including the need for the device to have direct contact with blood. U.S. Pat. No. 5,209,231 (Cote et al.) discloses a somewhat different approach which is to measure the rotation of a plane of polarized light through blood or another body fluid. This technique and others like it use a very small rotation (millidegrees) and hence produce a very small signal, making the method very sensitive to scattering, movement, and pathlength variability.

As mentioned earlier, although in theory, given enough signal to noise, one should be able to determine the concentration of the constituents through infrared spectroscopy, in practice, such determinations have been shown to be very challenging. Measurement of glucose, in particular has been shown to be very difficult, even on an in vitro basis. The reasons are several fold:

(1) The body tissue and blood in particular are primarily composed of water. Water has a very strong intrinsic absorption in the infrared (IR) region, particularly in the mid IR region. The strong absorption by water severely reduces the signal to noise ratio, unless pathlengths are kept quite small. In the mid and near IR regions, pathlengths must be down to approximately 25 um or 1000 um, respectively, to obtain an acceptable signal to noise ratio.

(2) The concentrations of the constituents are low compared to that of water. The spectra of the various constituents in blood and other body fluids tend to overlap with one another and that of water, and almost all of the concentrations of constituents vary over the physiological range. For example, in the measurement of blood glucose concentration, the measurement must be taken against a backdrop wherein the concentration of the other constituents is constantly changing and the spectra of the other constituents overlap that of glucose.

(3) In the near IR region, both positions of the peaks and intensity of the water spectra shift with temperature and pH, further complicating the measurement.

(4) Blood and other body tissues tend to scatter light substantially, further reducing the signal to noise ratio detected by a sensor and further adding variability.

Despite these difficulties, several researchers have been able to determine glucose and other constituent concentration with acceptable or near acceptable accuracy on an in vitro basis, using multivariate techniques for the analysis of the spectra. It should be emphasized that these measurements were done on an in vitro basis, with a state-of-the art spectrophotometer, with a well-optimized set-up, and generally with factors not possible to reproduce on an in vivo basis, (i.e., temperature stability, constant pathlength). In addition, these measurement typically required a large number of spectral points (>100) to obtain good accurate predictions of the constituent concentration. Hence, to make these measurements on an in vivo basis, extraordinary measures must be taken to ensure that the signal to noise ratio is the same or better as the in vitro measurements, and that there are no added additional artifacts.

Given the difficulty with in vitro measurements, it should come as no surprise that the transcutaneous means have not worked. In a transcutaneous sensor, the light "sees" a far large number of variables than what is seen on an in vitro basis due to the interaction of light with skin, fat, bone, and the like. Sorting out the spectra becomes very difficult. In addition, the signal to noise ratio obtainable with such a means is significantly lower than in vitro measurements due to substantially poorer optical coupling, the presence of additional scattering tissues (e.g., skin), and absorption by tissue which may not contain glucose (e.g., fat). Finally, given the accuracy necessary in the spectra to obtain an accurate determination of the constituent concentration, excessive artifacts are apt to obscure such measurements.

Attempts were made to eliminate some of the problems related to transcutaneous infrared sensor by using an implantable blood glucose sensor described in U.S. patent application Ser. No. 08/500,388, filed Jul. 6, 1995, entitled "IMPLANTABLE SENSOR AND SYSTEM FOR MEASUREMENT AND CONTROL OF BLOOD CONSTITUENT LEVELS". For example, this sensor improved the signal to noise ratio by implanting the sensor, thereby eliminating some of the sources of optical loss. The sensor in this patent application consists of spatially separated pairs of infrared light sources and infrared sensitive detectors. Each source and detector pair is spaced so that light from the source passes through a blood vessel and is received by the detector. Each source outputs a different discrete narrow band of light. The significant spatial separation between each source/detector pair causes a significant spatial separation of the spectral lines output by the sources. Each detector thus "sees" a different spatial region of the blood vessel. Due to this fact and the dynamic nature of blood vessels, it is believed that the spectral information output from the detectors cannot be used to obtain sufficiently accurate blood glucose levels.

Furthermore, the measurement technique in the above-described patent application fails to correct for spectral artifacts due to scattering and absorption by the blood vessel wall and any other tissue that may be in the optical path between the output of each source and the input of the corresponding detector. In addition, the diameter of a blood vessel is neither constant over time, since a blood vessel bulges and collapses with each heartbeat, nor uniform in diameter. In addition, blood is not spatially homogeneous, so there can be significant variability in scattering from point to point. Pathlength variability in the measurement techniques described in the above identified patent application may thus be on the order of 1 part in 100 (in absorbtivity units), which is large enough to destroy the usefulness of the spectral information obtained therefrom.

Many of the problems discussed above also arise when measuring other body fluid constituents. In sum, there are considerable obstacles to obtaining accurate in vivo measurements of body fluid constituents. Despite a long-felt need, sensors and spectral analysis techniques heretofore have been inadequate for this task. The present invention fulfills such a need and provides both sensors and spectral analysis techniques which yield accurate in vivo measurements of body fluid constituents.

BRIEF SUMMARY OF THE INVENTION

The present invention provides methods and apparatus for determining concentration of constituents of body fluids in a mammal using in vivo spectroscopy. A sensor system is implanted in the mammal. The sensor system includes a source of light which emits at a plurality of different wavelengths and a detector for detecting light emitted from the source. At least one of the wavelengths is in the infrared region. The source and the detector are arranged so that the light output from the source interacts with a body fluid before being received by the detector, and so that the light from light from the plurality of different wavelengths has a substantially collinear optical path through the fluid with respect to one another. A signal is obtained at the output of the detector which contains spectra of the body fluid at each of the plurality of different wavelengths. A processor analyzes the signal to determine the concentration of at least one constituent of the body fluid.

The sensor may be disposed extravascularly to measure concentration of blood constituents. Alternatively, the sensor may be disposed within interstitial fluid or gel to measure concentration of a constituent of the interstitial fluid or gel, or the sensor may be disposed around a vascular membrane to measure concentration of a constituent of blood in the membrane.

In another embodiment of the invention, a medication dispenser is connected to the sensor for dispensing doses of medicine in response to the concentration of the chemical constituent output from the processor.

To minimize artifacts when measuring fluid constituents in a blood vessel such as a vein, light from the plurality of different wavelengths is emitted in a substantially single period of time and the spectra is corrected for extraneous tissue in the optical path between the source and the detector.

BRIEF DESCRIPTION OF THE DRAWINGS

The following detailed description of preferred embodiments of the invention will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 2 is a schematic diagram of a source which may be used in the sensor of FIG. 1;

FIG. 3C is a sectional view of a second physical implementation of a device for mounting implantable portions of the sensor of FIG. 1 thereon, as the device appears attached to a vein;

DETAILED DESCRIPTION OF THE INVENTION

The present invention is based on the discovery that the concentration of a chemical constituent of body fluid may be accurately detected in vivo by directing electromagnetic radiation or light energy (hereafter, "light") containing a plurality of different infrared wavelengths, and particularly, near-infrared wavelengths, through the body fluid so that the light of the plurality of different wavelengths forms a substantially collinear path with respect to each other as they pass through the fluid. It has been further discovered that the concentration of glucose is one chemical constituent of body fluid that may be accurately detected in this manner, and that the glucose level may be measured within a blood vessel (e.g., vein), within a vascular membrane, or within interstitial fluid or gel (hereafter, "interstitial fluid"). It was further discovered that to obtain accurate concentrations of chemical constituents of body fluids, such as glucose, in rapidly changing anatomical structures such as veins or vascular membranes, it is necessary to emit and detect all of the different wavelengths of light in a substantially single period of time.

Figure 1:
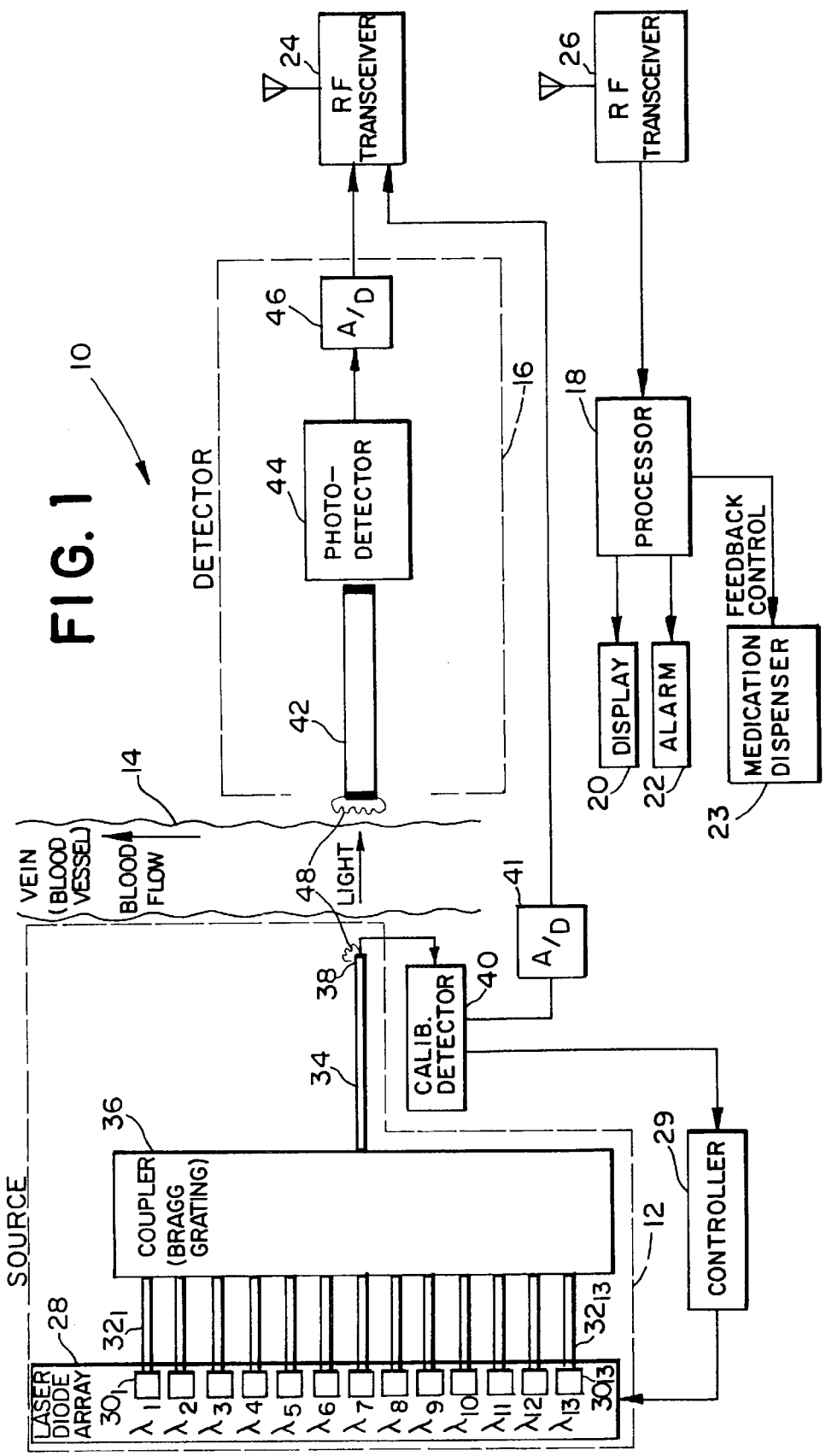
FIG. 1 is a schematic diagram of an in vivo sensor in accordance with one preferred embodiment of the present invention.
Figure 3A:
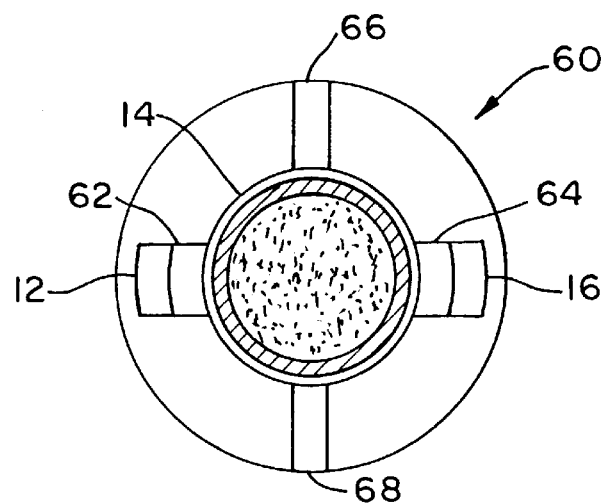
FIG. 3A is a sectional view of a first physical implementation of a device for mounting implantable portions of the sensor of FIG. 1 thereon, as the device appears attached to a vein.
Figure 3B:
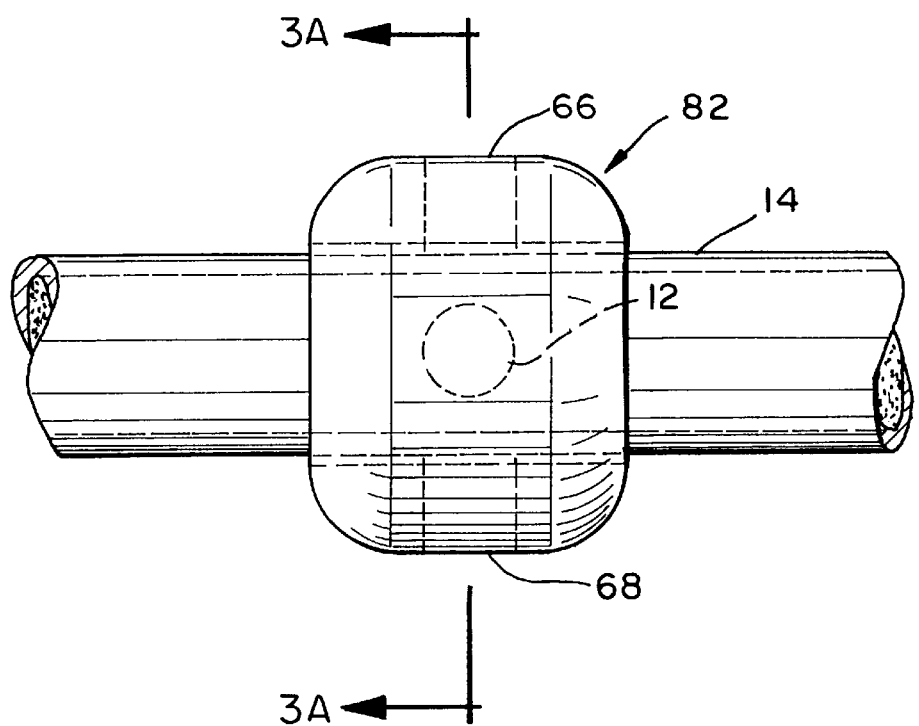
FIG. 3B is a side elevational view of the device of FIG. 3A.

FIG. 1 is a schematic block diagram of an implantable sensor system 10 for analyzing chemical constituents of body fluids in a mammal, in accordance with a first embodiment of the present invention. This embodiment detects the concentration of a chemical constituent in blood flowing through a vein, and is particularly useful for detecting the concentration of blood glucose levels. The physical structure of one embodiment of the sensor system 10 is shown in FIGS. 3A–3C, discussed below. The components shown in the figures are not to scale.

Referring to FIG. 1, the sensor system 10 includes (i) a light source 12 for emitting at a plurality of different infrared wavelengths into vein 14, (ii) a detector 16 for detecting light emitted by the light source 12 and which has interacted with the blood in the vein 14 and outputting a signal which contains spectral information of blood constituents, and (iii) a processor 18 for analyzing the spectral information contained therein, and determining the concentration of at least one chemical constituent in the blood from the spectral information. A display 20 and an alarm 22 are connected to the processor 18 for receiving display data and alarm conditions from the processor 18 based on the determined concentration. The output of the processor 18 may optionally be used for feedback control, such as to automatically control a medication dispenser 23. One type of medication dispenser 23 may be an externally mounted or internally implanted insulin infusion pump.

The light source 12 and detector 16 are positioned extravascular and are arranged opposite to, and facing each other, and so that the output of the light source 12 goes through approximately the center of the vein 14. The output of the light source 12 and the input of the detector 16 are in close proximity to, or in contact with, the outer wall of the vein 14, as described in more detail with respect to FIG. 2. In one suitable embodiment of the invention wherein the diameter of the vein 14 is between 0.3–1.0 mm, the distance between the output of the light source 12 and the vein wall, and the distance between the input of the detector 16 and the vein wall is less than 100 $\mu$m (0.1 mm).

Depending on the needs of the patient and the sophistication and miniaturization of the system components, some or all of the components of the sensor system 10 are implanted. In FIG. 1, the light source 12 and the detector 16 are implanted in the person, and the processor 18 is external to the person. For example, the processor 18 may be worn on a person's wrist or belt. The implanted components communicate with the external components via suitable telemetry circuitry, such as a pair of RF transceivers 24 and 26 associated with the implanted and non-implanted components, respectively. Alternatively, the processor 18 may be implanted and connected directly to the output of the detector 16, and the display 20 and alarm 22 may be external to the person. In this configuration, the processor 18 may communicate with the display 20 and alarm 22 via RF transceivers connected respectively to the output of the processor 18 and the inputs of the display 20 and alarm 22. If the output of the processor 18 is used for feedback control, the medication dispenser 23 may be either external or internal to the person.

An important feature of the invention is the light source 12 which outputs light at a plurality of different infrared wavelengths, wherein the light from the wavelengths have a substantially collinear optical path with respect to one another. Collinearity is important because the sensor 10 must detect relative differences in absorptivity of the order of one part in $10^4$ from one wavelength to the next in order to measure relatively dilute substances in a body fluid, such as glucose in blood. If the optical paths are not substantially collinear, variations in scattering, absorption, or pathlength differences may obscure the desired spectral information.

FIG. 1 shows one preferred light source 12 for producing such an output which is particularly useful in measuring concentrations of blood glucose.

The light source 12 contains a light emitting device 28 in the form of a laser diode array which has a plurality of individual laser diodes, such as thirteen individual laser diodes $30_1$–$30_{13}$. Each laser diode 30 produces a discrete wavelength $\lambda_1$–$\lambda_{13}$. At times, it may be necessary to spectrally filter the output of one of the diodes to obtain a more spectrally pure output. The state of the light emitting device 28, including the state of the individual laser diodes $30_1$–$30_{13}$ is controlled by a controller 29. The output of each laser diode 30 is coupled to an input of a respective single-mode optical fiber $32_1$–$32_{13}$, having a core diameter of about 9 μm. The output of the respective optical fibers $32_1$–$32_{13}$ are coupled to an input of one single-mode optical fiber 34 of a similar construction and core diameter as the optical fibers 32, via a Bragg diffraction grating coupler 36 or a wavelength division multiplexer/demultiplexer. At the output of the coupler 36, light from all of the individual wavelengths is substantially collinear. This coupling technique thus ensures that light at each wavelength has the identical optical path as that of every other wavelength.

The output of the one optical fiber 34, labeled as 38, is the output of the light source 12. A portion of the output of the one optical fiber 34 is diverted to a calibration detector 40 via a beam splitter (not shown) for use by the processor 18 in calibrating the output of the laser diodes $30_1$–$30_{13}$. The output of the calibration detector 40 is then fed into a preamplifier (not shown) an analog-to-digital (A/D) converter 41, and finally to the RF transceiver 24. Optionally, the output of the calibration detector 40 may also be connected to the controller 29 for adjusting the power output of the light emitting device 28 (in FIG. 1, the laser diode array) to produce constant output power from pulse to pulse. One suitable calibration detector is an InGaAs detector with a two stage preamplifier. A simple temperature measuring device may at times be used to gauge the output of each of the diodes $30_1$–$30_{13}$, instead of the calibration detector 40.

For detecting the concentration of glucose in blood to an accuracy of ±18 mg/dl over the physiological range of temperature, pH and blood chemistry, it is sufficient to use about thirteen different wavelengths, wherein two wavelengths (or more) are used to normalize pathlength variations, one wavelength is used for baseline offset, and the remaining ten wavelengths are used for the glucose measurement. With an accurate measurement of the temperature of the body fluid, it might be possible to reduce the number of wavelengths. Ideally, the two wavelemgths chosen for pathlength normalization are not affected by "extraneous" tissue surrounding the fluid desired to be measured (in this case, blood). That is, the difference in absorptivity between the two wavelengths is not affected by "extraneous" tissue. One set of wavelengths (in nanometers) suitable for detecting the concentration of glucose in blood when the blood pathlength is 0.5 mm or less are as follows:

1300, 2259, 1964, 2038, 1970, 2146, 1376, 2084, 1391, 2186, 1434, 2154 nm

The first wavelength (1300) is used for baseline offset and the next two wavelengths (2259 and 1964) are used for pathlength normalization.

If longer pathlengths are used, the optimum wavelengths shift somewhat towards shorter wavelengths. Alternatively, wavelengths further into the infrared region or into the visible region may be useful for detecting other chemical constituents. Thus, there may be some wavelengths which are not in the infrared region. The specific number and value of wavelengths depends upon the constituent of interest and the desired accuracy of the concentration. In general, however, it is preferable to avoid spectral regions of high water absorption. Accordingly, the near-infrared region is generally preferred over the middle infrared region.

The particular wavelengths and spectral regions chosen are determined on a reiterative, semi-trial and error basis in conjunction with the determination of an in vitro algorithm (discussed below), taking into consideration the absorption peaks of the constituents of interest, water absorption, hardware considerations, and other consideration such as other possibly interfering tissues. In the case of the glucose sensor, the region between 900 nm and 2,500 nm was chosen, since wavelengths above 2,500 nm suffered from excessive water absorption and device limitations, and wavelengths below 900 nm suffered from excessively weak absorption. With this in mind, blood samples from over 450 people were taken and an FT-IR spectra between 900 nm and 2,500 nm was taken on each of these samples.

There are a number of well-known techniques to obtain correlation of the spectra and the measured constituent values, including the Norris Regression Algorithm, Partial Least Squares, Principal Component Regression, and Neural Networks. Various of these techniques were attempted on the blood samples of 450 people on a semi-trial and error basis to achieve the following goals:

1. Obtain the best cross-validation, calibration, and predictive standard errors.
2. Use as few wavelengths as possible.
3. Use as short wavelengths as possible.

Each of these algorithms ultimately yield the choice of wavelengths and the corresponding algorithm which correlates the measured spectra to the constituent concentration. The section below entitled: "DETERMINATION OF THE IN VITRO ALGORITHM" discusses the optimization of this algorithm using the Norris Regression, which is the preferred embodiment of the invention.

For measuring the concentration of glucose in blood in the preferred embodiment, each laser diode 30 should output sufficient power to deliver at least 1 mW to the photodetector 44. Typically, this implies that the source output should be at least 10 mW at about 2,200 nm.

The detector 16 includes a collection optical fiber 42 located on the other side of the vein 14, diametrically opposite the output of the light source 12, to collect the light emitted from the light source 12 after it has traversed the vein 14. The collection optical fiber 42 has a larger core diameter than the light source output fiber 34, optimally from about 0.2 to about 1.0 mm, depending upon the size of the vein used for measurement and whether or not the vein is compressed by the sensor 10. The collection optical fiber 42 must be chosen to have good collection properties. Thus, it should ideally have a numerical aperture (NA) of 0.39 or larger when measuring a highly scattering fluid such as blood. A large diameter core is also preferable for the collection optical fiber 42 in terms of collection efficiency and hence signal to noise. However, a fiber that is too large may cause non-linearities due to pathlength differences (through the vein) of the light collected by different areas over the aperture of the collection optical fiber 42 or photodetector 44 (discussed below). The output of the collection optical fiber 42 is fed into a photodetector 44, such as an uncooled InGaAs detector with a two stage linear preamplifier. The photodetector 44 and the preamplifier should have (1) a high degree of linearity, (2) a high signal to noise ratio, and (3) a sufficiently wide spectral bandwidth to detect the entire spectral band of the source 12. To accurately measure glucose absorptivity, the optical power readings taken by the photodetector 44 must be $10^5$ greater than the noise level, and therefore the photodetector 44 must be linear over 5 decades. When using infrared wavelengths, a 5 decade requirement leaves very little room between the noise threshold on one hand and the level of linearity on the other hand. No spectral filter is required in front of the photodetector 44 unless the photodetector can detect wavelengths longer than 3,000 nanometers, where black body radiation becomes significant. In the preferred embodiment of the invention, a electronic bandpass filter (not shown) is used to limit 1/f noise and high-frequency noise. The electronic bandpass filter will typically cut-out at a frequency from about ½T to about 2/T, where T is the pulse width of any laser diode pulse. The photodetector 44 is preferably a single element device which is sensitive over the entire range of received infrared wavelengths.

The output of the photodetector 44 is sent to an A/D converter 46, and the digitized output signal is transmitted by the RF transceiver 24, received by the external RF transceiver 26 and sent to the external processor 18. The RF transceivers 24 and 26 preferably have a range from about one to about three meters. Alternatively, the transceivers 24 and 26 may be replaced by infrared transceivers.

In some cases, no collection optical fiber 42 is necessary. Instead, the photodetector 44 may directly detect the light after it has passed through the vein 14. One advantage of using a collection optical fiber to receive the light is that it is relatively light in weight and small in size compared to the photodetector 44, and therefore may be less likely to cause the vein to become non-patent. A collection optical fiber also may be less prone to build-up of encapsulation tissue than a photodetector 44 since it is easier to mechanically secure an optical fiber than a photodetector with respect to a vein, and hence avoid chafing.

The output of the calibration detector 40, after being amplified and digitized, is connected to the RF transceiver 24 for transmission to the processor 18. The processor 18 thus receives a signal from the calibration detector 40, as well as from the collection detector 16. The processor 18 uses the measured power of both signals to make certain corrections, as discussed below.

Whenever a foreign object is implanted in a living body, tissue tends to build up on the object, even when the object is made of a biocompatible material. This tissue is known as "encapsulation tissue." Encapsulation tissue usually builds up over time to a certain amount and then stops growing and reaches a steady state, typically within 4–6 weeks. In FIG. 1, encapsulation tissue 48 is shown on the output 38 of the optical fiber 34 and on the input of the collection optical fiber 42. In the preferred embodiment of the invention, the optical fibers 32 and 34 may be encased in a hermetic and biocompatible jacket, with an infrared window such as sapphire at the exposed ends. The jacket and window may be coated with a hydrogel or similar material to minimize growth of encapsulation tissue. The jacket may be constructed of titanium or stainless steel or another hermetic and biocompatible material. While such measures are helpful to minimize rejection and the growth of encapsulation tissue, such tissue may likely form on exposed surfaces and must be accounted for when analyzing spectral information.

When taking measurements in rapidly moving anatomical structures such as pulsating veins, it was also discovered that to obtain an accurate measurement, the spectra must be taken at a "substantially single period of time" (i.e., the spectra must be substantially temporally coincident). This requires that the plurality of diodes at different wavelengths be pulsed within a "substantially single period of time". In particular, the spectra should be taken in a time short enough so that signal due to pathlength variations over the measurement time is much smaller than the anticipated signal of the fluid constituent. Experimental data shows that the "substantially single period of time" in veins and the like should be less than about 100 $\mu$sec for the measurement of blood glucose. Thus, as defined herein, a "substantially single period of time" does not mean simultaneous, but rather means a time period short enough to be substantially simultaneous with respect to changes that are occurring to the fluid constituent in the measured space. For measurements taken in anatomical structures which do not experience rapid change, such as interstitial fluid or gel, longer time periods are acceptable.

In operation, each diode 30 of the laser diode array is pulsed sequentially for a fixed period time, with an off period between the different diode pulses. In one embodiment of the invention suitable for measuring the glucose concentration in blood, a pathlength change of about 10% over one second may be expected in certain veins as the vein pulsates due to blood flow. A glucose concentration of 100 mg/dl contributes in a 0.5 mm pathlength of blood an absorption of the order of $0.7 \times 10^{-4}$ at 2,273 nm, one of the strongest glucose bands in the near-infrared range. If two consecutive wavelength measurements having an accuracy of one part in $10^5$ is desired, the measurements must be taken within 0.1 milliseconds of one another to obtain a temporally coincident measurement. That is, the entire spectra must be taken within 0.1 milliseconds. In one embodiment of the invention which meets this criterion, each diode 30 is pulsed sequentially for about 3 $\mu$sec, with an off period of about 3 $\mu$sec between the different diode pulses. Thus, a thirteen wavelength embodiment requires about 75 $\mu$sec (0.075 milliseconds) for a complete cycle of pulses. The diode pulsing is controlled by the controller 29.

To further minimize temporal artifacts, diode pairs 30 which are very close together in wavelength or which are used for pathlength calibration should be pulsed in sequence one after the other. For the sample wavelengths listed above, the diodes 30 at pathlength calibration-related wavelengths 1,964 nm and 2,259 nm are pulsed next to one another, as are the diodes 30 at close wavelength pairs 1,964 nm and 1,970 nm, and 2,154 and 2,146 nm.

To improve the signal to noise ratio, it is acceptable to take a number of repeated spectra N, over a relatively short period of time. The time period should be short enough so that there is no appreciable change in the constituent concentration. For a glucose sensor, this period of time might be several minutes. The processor 18 would then either average the N spectra, or would compute the constituent concentration and then average the N predicted values of constituent (s). Such a scheme provides a square-root N improvement in signal to noise. If there are changes in pathlength, pH, or temperature, over the N samples, it is generally preferable to average the predicted concentration of the constituents as opposed to averaging the spectra and then predicting the concentrations.

In FIG. 1 (and FIGS. 3C, 4C, and 5–7 discussed below), the optical fibers 34 and 42 function as a light delivery system for the active elements of the source 12 and the detector 16, and also provide flexibility in arranging the sensor components within its housing. Likewise, in FIG. 2, the optical fiber 54 provides a similar function for delivering light. If other means are used to adequately optically mix the light from the plurality of different source wavelengths, one or all of the optical fibers 34, 42 and 54 may be eliminated and light may be directly emitted or received by the active respective sensor components. For example, the output of the coupler 36 may be directly emitted into the vein 14, and the photodetector 44 may be arranged to directly receive emitted light which passes through the vein 14. Nonetheless, the preferred embodiment of the invention uses optical fibers to deliver the light to active sensor components.

FIG. 2 shows an alternative embodiment of a light source 12'. In this embodiment, the light output from the laser diode array become collinear by mixing of the beams in a long optical fiber. Specifically, the outputs of the individual laser diodes $30_1$–$30_{13}$ are fed into individual multimode optical fibers $50_1$–$50_{13}$. One suitable multimode fiber 50 has a core diameter of about 100 μm, and forms a fiber bundle 52 having a diameter of about 0.5 mm. The output of the multimode fiber bundle 52 is fed into the input of a single core multimode optical fiber 54 of approximately the same diameter as the fiber bundle 52. The single core multimode fiber 54 has a significant length, such as a length greater than 1 meter, to allow substantial wavelength mixing to occur as the light beams travel toward the output. (Although reference is made to "wavelength mixing", the individual diodes are pulsed sequentially and not simultaneously.) To minimize the space required by the long optical fiber 54, the fiber 54 may be coiled in tight loops.

Referring to FIG. 1, the single-mode optical fiber 34 need not have any significant length because the wavelength mixing occurs in the coupler 36, and thus the light of the plurality of wavelengths are already mixed at the input of the optical fiber 34. The detector used for the embodiment of FIG. 2 is not shown, but it should have a similar diameter as the optical fiber 54.

FIG. 3A shows a sectional view of a first embodiment of a ring-like device 60 for mounting implantable portions of the sensor system 10 thereon and for maintaining a fixed relationship between the output of the light source 12 and the input of the detector 16. FIG. 3B shows a side elevational view of the sensor of FIG. 3A. Both the source 12 and the detector 16 are hidden from view in FIG. 3B. The source 12 is shown in phantom in FIG. 3B. Referring to FIGS. 3A and 3B, the vein 14 extends through the center of the device 60. The device 60 is preferably constructed of titanium or another suitable biocompatible material. The light source 12 and the detector 16 are mounted in a pocket of the device 60, and their respective outputs and inputs are protected by windows 62 and 64 of biocompatible and infrared transmissive material, such as sapphire. The windows 62 and 64 and ring-portion of the device 60 may be coated with a hydrogel or another polymer to minimize growth of encapsulation tissue. To further inhibit the growth of encapsulation tissue, the device 60 should be designed to minimize sharp edges. The device 60 may be constructed in two C-shaped halves which are connected together at joints 66 and 68 after placement around the vein 14.

As discussed above, the source light may be directly emitted into the vein 14, and directly detected by respective active sensor components, or optical fibers may be used as a light delivery system for the active elements of the source 12 and the detector 16. FIG. 3A shows the direct emission implementation. FIG. 3C shows a second embodiment of a mounting device 82 which uses the light delivery system implementation wherein the output and input ends of the optical fibers 34 and 42, respectively, are mounted to the device 82. In the light delivery system implementation, the active components of the device 82, including the light emitting source 28 and photodetector 44, are located remotely from the device 82.

Figure 4A:
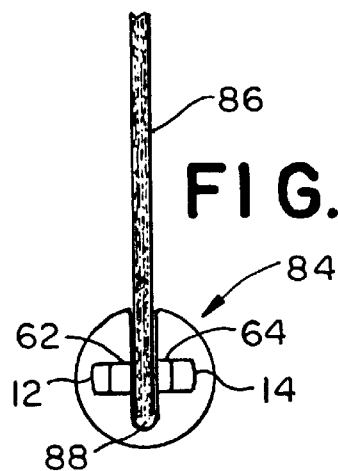
FIG. 4A is a sectional view of a third physical implementation of a device for mounting implantable portions of the sensor of FIG. 1 thereon, as the device appears attached to a vascular membrane.
Figure 4B:
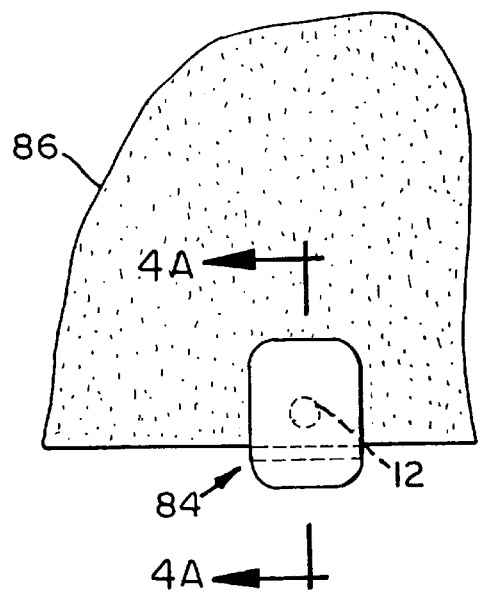
FIG. 4B is a side elevational view of the device of FIG. 4A.
Figure 4C:
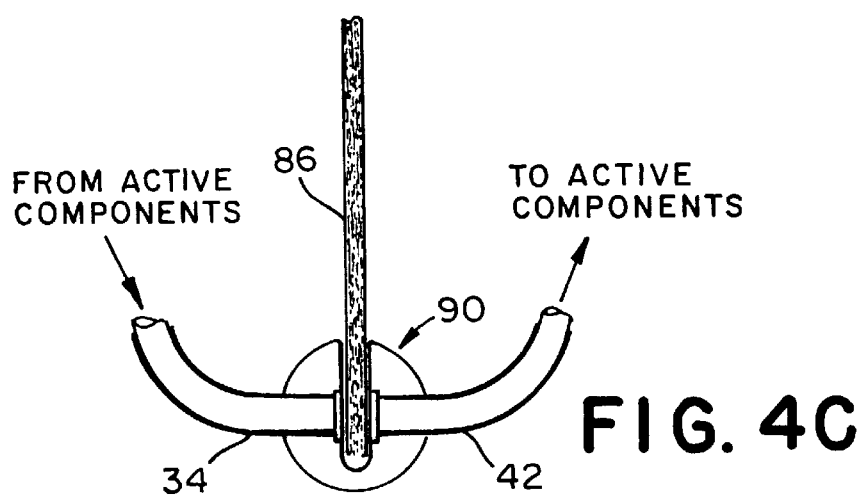
FIG. 4C is a sectional view of a fourth physical implementation of a device for mounting implantable portions of the sensor of FIG. 1 thereon, as the device appears attached to a vascular membrane.

The sensor 10 may also be used to measure concentration of a constituent of fluid in a vascular membrane, such as the peritoneal membrane. FIG. 4A shows a sectional view of a third embodiment of a direct emission device 84 for use with a vascular membrane 86. FIG. 4B shows a side elevational view of the sensor of FIG. 4A. Referring to FIGS. 4A and 4B, the device 84 is generally U-shaped as oriented in FIG. 4A (C-shaped if rotated 90 degrees to the left or right), and thus defines a slot 88. The vascular membrane 86 is disposed in the slot 88. Implantable portions of the sensor system 10 are mounted in pockets of the device 84 on either sides of the slot 88. The device 84 thus maintains a fixed relationship between the output of the light source 12 and the input of the detector 16. The device 84 may include the same coatings and windows 62 and 64, and may be constructed of the same materials, as the device 60 of FIG. 3A. Unlike the device 60 which requires a two piece housing portion, the housing portion of the device 84 may optionally be constructed from a single unitary piece of U-shaped material. FIG. 4C shows a fourth embodiment of a device 90 for use with a vascular membrane 86 which uses the light delivery system implementation, wherein the output and input ends of the optical fibers 34 and 42, respectively, are mounted to the device 90.

Referring to FIGS. 1 and 2, the light source 12 may use any light emitting device 28 which provides an output of light at the requisite power, wavelengths and spectral sharpness. Glucose is a dilute constituent of blood. Due to this fact, when measuring the concentration of glucose in blood, there are a limited number of light emitting devices that meet all of these criteria and which have acceptable efficiency.

Light emitting diodes (LEDs) are one suitable light source which may be used in place of one or more of the laser diodes 30. Some LEDs may require a spectral filter, such as a narrow band filter, while others may be used without a spectral filter. A disadvantage of LEDs is that they are less efficient than laser diodes, particularly after the requisite spectral filtering is provided. In addition, LEDs are high divergence devices and are difficult to couple to an optical fiber with efficiencies much greater than 20%. Some advantages of LEDs over laser diodes are that they are inexpensive and the entire spectrum from 800 nm through 2,500 nm is commercially available.

Perhaps the most important decision in the design of an infrared spectroscopic chemical sensor is the choice of spectral region(s) and wavelengths, particularly if a white light source is either impractical or substantially non-optimal. The choice of wavelengths and spectral region(s) ultimately determines both the hardware and the algorithm. For an in vivo set-up, in general, the absolute minimum number of wavelengths is three points (unless one can use other means to pull out background and scattering and absorption by other constituents, such as using the pulsatile component as in the pulse oximeter). At least one point is needed for pathlength calibration and another two points are needed for measuring the height of the absorption peak. In complex media, such as blood, where there are a number of overlapping constituents, the number of requisite wavelengths increase substantially. As a general rule, one can expect to add one or two spectral points for each chemical constituent whose concentration varies independently and which has some spectral structure in and around the absorption peak(s) used for determination of the constituent of interest. For near IR determination of the concentration of blood glucose, one needs additional spectral points to compensate for the overlapping globulin, cholesterol, albumin, urea, hemoglobin, uric acid, and of course, water. In addition, there are no doubt other chemical species for which one also has to compensate. The means to choose the wavelengths are discussed below.

The selection of the spectral region(s) to be emitted by the source 12 depends upon the fluid constituent being measured, the availability of light sources and suitable detectors, water absorption and noise considerations. In general one chooses spectral regions in the vicinity of the absorption band(s) of the constituent(s) being measured. For example, the strongest glucose bands are around 10,000 nm, followed by the bands at about 2240 and 2080 nm, finally followed by a still weaker band at 1600 nm. Many other blood constituents show similar absorption patterns. On the other hand water absorption and device constraints, particularly the availability of diodes and uncooled sensitive detectors, become very problematic beyond 2,500 nm. As discussed above, the photodetector 44 must have a five decade dynamic range to accurately determine glucose. For an implantable device which cannot be cryogenically cooled, the linearity requirement mitigates against the use of wavelengths above 3,000 nm for constituents of low concentration since uncooled detectors do not have suitable performance characteristics above this wavelength.

Furthermore, water absorption becomes substantially more problematic beyond 2,500 nm. Light energy at 10,000 nm experiences more than a 10 dB loss through a water layer of 0.1 mm, thereby making it very difficult to obtain an acceptable signal to noise ratio for an implantable device. Hence, for the measurement of glucose as well as most other blood constituents, it is generally preferable to use light less than 2,500 nm, even though there is substantial spectral information beyond 2,500 nm for most blood constituents. Even below 2,500 nm, there are some bands of water absorption which can cause excessive attenuation for longer pathlengths; one at 1,899 nm and another at 1,454 nm.

Figure 5:
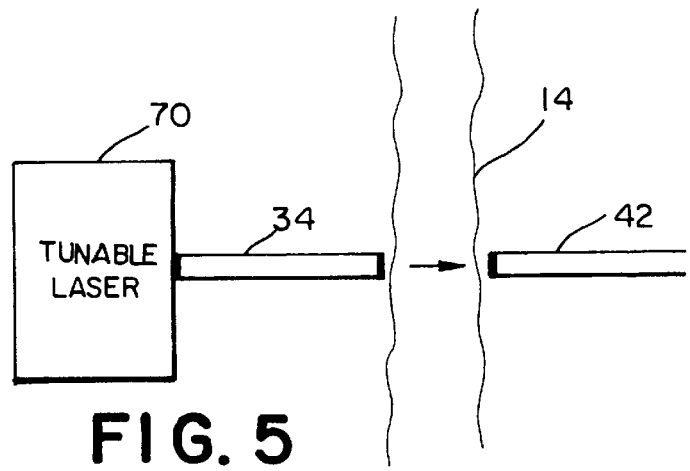
FIG. 5 is a schematic diagram of source having a single output which may be used in the sensor of FIG. 1.

Referring to FIG. 5, the light emitting device 28 of FIG. 1 may also be a tunable laser 70 which is programmed to produce a repeating output at the desired wavelengths. A tunable laser inherently outputs collinear light with respect to the plurality of wavelengths because there is only a single output. Thus, the output of the tunable laser 70 may be coupled directly into the input end of optical fiber 34 of FIG. 1. As with the laser diode array 28, the entire desired spectra should be taken within substantially the same period of time. The calibration detector 40, collection detector 16, processor 18 and related components are not shown in FIG. 5 and may be the same components as those of FIG. 1.

Furthermore, the light emitting device 28 may be a white light source, such as a white light source having maximum output power in the near-infrared region. A white light source also inherently outputs light having wavelengths which are collinear with each other because there is only a single output. Thus, the output of the white light source may also be coupled directly into the input end of optical fiber 34 of FIG. 1. When using a white light source, it is necessary to spectrally separate the output of the white light source to obtain spectral information for desired wavelengths. In one technique, shown in FIG. 6, a tunable spectral filter 72 is disposed between white light source 74 and the photodetector 44, such as between the output of the white light source 74 and the input end of the optical fiber 34. The tunable spectral filter 72 is programmed to produce a repeating output at the desired wavelengths. As with the laser diode array 28, the entire desired spectra must be taken over a substantially single period of time. To conserve energy, the white light is pulsed on only when it is desired to take a spectra. The tunable spectral filter 72 may be implemented by either a rotating disk with various spectral bandpass optical filters or by a rotating grating which couples the desired spectra into the optical fiber 34.

Figure 7:
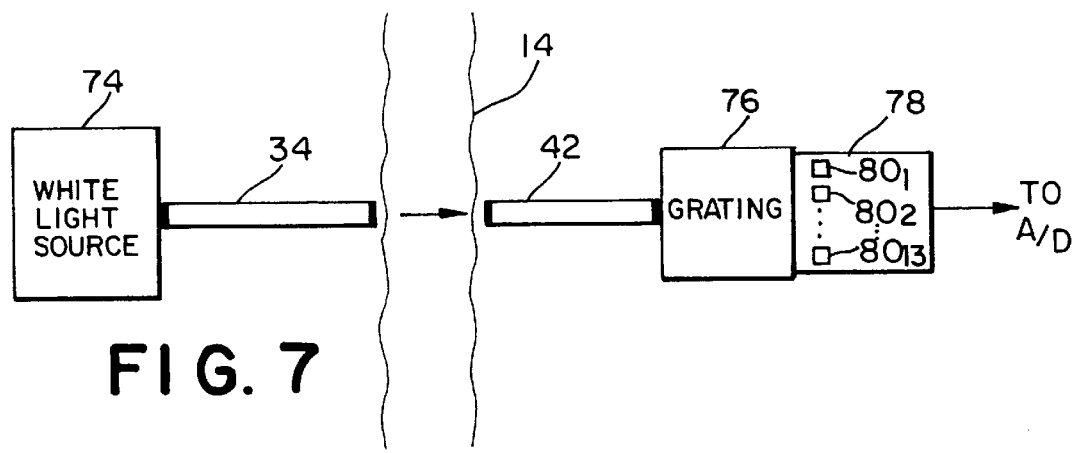
FIG. 7 is a schematic diagram of an alternative source and detector arrangement for use in the sensor of FIG. 1.

In another technique, shown in FIG. 7, a fixed grating 76 is disposed at the input of a photodetector 78 to spectrally separate the broadband white light into different spatial packets related to the thirteen wavelengths. (The photodetector 78 replaces the photodetector 44 in FIG. 1.) The photodetector 78 is constructed of an array of photodetectors $80_1$–$80_{13}$, wherein each photodetector 80 detects one of the thirteen wavelengths. Since each photodetector $80_1$–$80_{13}$ in FIG. 7 is coupled to the same collection optical fiber 42, the requirement that light at each wavelength spatially overlaps each other is met.

Figure 6:
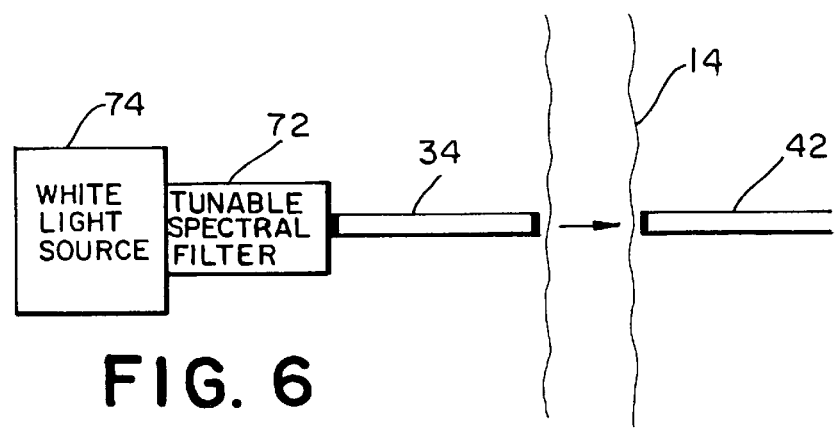
FIG. 6 is a schematic diagram of another single output source which may be used in the sensor of FIG. 1.

The sensors in FIGS. 5 and 6 include similar calibration detector, collection detector and processor components as in FIG. 1. Only the collection optical fiber 42 is shown in these figures. Likewise, the sensor in FIG. 7 includes similar calibration detector and processor components as in FIG. 1. The collection optical 42 fiber in these figures is a multi-mode fiber, typically having a diameter of 0.5 mm or greater, if non-linearity due to pathlength variations over the fiber aperture do not present a problem.

Light having a plurality of different wavelengths which traverse substantially the same optical path (and which are thus collinear) is most easily produced by the source configuration of FIG. 1 wherein a plurality of single mode fibers are coupled to one single mode fiber via a Bragg diffraction grating. The amount of spatial overlap of the light required amongst the various wavelengths with respect to one another is a function of how strong a signal is produced by the desired fluid constituent and the expected degree of spatial inhomogeneity. Blood and most other human tissue tends to be highly spatially inhomogeneous, primarily due to scattering. For example, a 1 mm path of blood with a 100 mg/dl glucose concentration produces a peak absorption on the order of $10^{-4}$ at 2,273 nm (due to the glucose). Two wavelengths, separated by 0.1 mm could create an apparent signal of $3 \times 10^{-4}$ if the variations in scattering are on the order of 1% per mm. For example, if there is a spatial variation in scattering of the order of 1% per mm, and two wavelengths of light are separated by 0.1 mm, the detector 16 would have difficulty seeing the glucose absorption peak over the variability in scatter.

As discussed above, a white light source does not present a problem with respect to collinearity, but care must be taken to ensure that the spatial relationship between the source and the detector is constant during the time a spectra is taken.

Other techniques may be used to produce the desired collinear source beam from LEDs or individual laser diodes without using gratings or long optical fibers. For example, the LEDs or laser diodes may be physically located very close to each other so that the optical path of each wavelength of light is substantially collinear with each other with respect to the fluid that receives the light. Also, a negative lens or aperture may be used to improve collinearity.

In an alternative embodiment of the invention, each individual light source in the light source 12 may be frequency modulated at a unique predetermined frequency. If a frequency modulation scheme is used, all of the individual light sources may be pulsed simultaneously, thereby guaranteeing that the output of the light source 12 is temporally coincident amongst the plurality of wavelengths.

The sensors of FIGS. 1–7 are extravascular, although they may be used intravascularly. However, intravascular sensors are not preferred because of potential clinical and technical complications, such as thrombosis and rejection. Alternatively, the sensors could be placed within a bone. However, the threat of infection is much greater in bone than in other internal body locations.

The sensors of FIGS. 1–7 are arranged to measure light from the source which passes directly through the vein 14 or other anatomical structure. However, the sensors may also be arranged to detect reflected or scattered light, or combinations of transmitted, reflected or scattered light. It is currently believed that precise coupling between the source 12 and the sample to be measured (vein 14 in FIG. 1) is more critical when relying upon reflected measurements than transmission measurements.

It is also believed that the signal to noise ratio obtainable with reflection spectroscopy in the measurement of blood glucose is lower than that obtainable with transmission spectroscopy in the near-infrared region.

The sensors of FIGS. 1–7 are suitable for a wide range of in vivo environments, such as veins, vascular membranes, muscles, arteries and the like. To obtain accurate in vivo measurements of fluid constituents from certain types of environments, it may be necessary to protect the sensor components (especially the source output and detector input) and/or the sensing area from exposure to unwanted constituents, particularly when measuring fluid constituents in interstitial fluid.

It is known that glucose concentration in interstitial fluid may be accurately correlated with blood glucose levels and used for diabetes control and management. For example, it is known that glucose levels in interstitial fluid lag glucose levels in blood by about 20 minutes. When measuring glucose concentration, interstitial fluid has many advantages over blood. Interstitial fluid and gel have little or no hemoglobin and red blood cells, both of which create artifacts in spectroscopic measurements. For example, red blood cells cause scattering. By measuring in interstitial fluid, other sources of potential artifacts present in blood measurements may also be eliminated, including artifacts from pulsating blood vessels and the confusion of glucose spectra with hemoglobin spectra. Pathlength variability is not as significant in measurements taken in interstitial fluid, as opposed to blood measurements. Interstitial fluid may also have a lower protein concentration than blood, thereby making it easier to discern glucose from the blood spectra with greater predictive accuracy. Fewer source wavelengths are thus required to obtain accurate concentrations.

Figure 8:
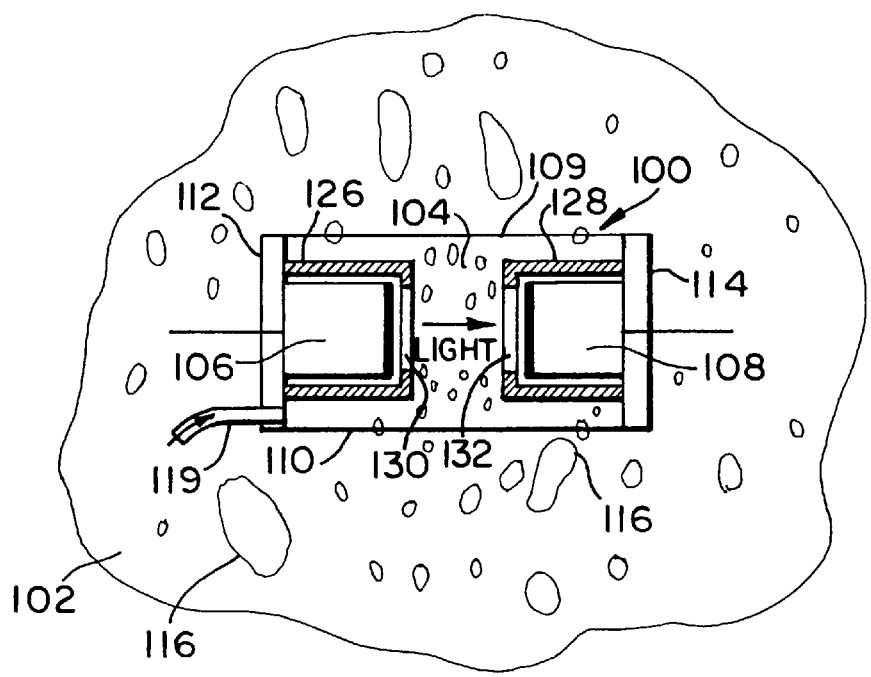
FIGS. 8 and 9 are schematic diagrams of in vivo sensors in accordance with additional embodiments of the present invention which are particularly useful for measuring within interstitial fluid or gel.

FIG. 8 shows a sensor 100 suitable for use in monitoring a fluid constituent in interstitial fluid 102. Interstitial regions contain interstitial gel consisting of interstitial fluid and a solid material primarily composed of collagen fibers. At times, debris may float within the interstitial region. The debris, adjacent tissue and solid material (hereafter, "tissue and debris") may reduce the accuracy of measurements if they enter the measurement zone. The sensor 100 is constructed to block such constituents from entering a measurement zone or chamber 104 between a source 106 and a detector 108. The sensor 100 includes a barrier or jacket 109 having a wall or barrier 110 and end caps or lids 112, 114. The wall 110 is constructed of an inert biocompatible material having a porosity selected to allow the interstitial fluid and gel to pass therethrough (good interchange of fluid), while blocking adjacent tissue and debris. Suitable materials for constructing the wall 110 include polytetrafluoroethylene (e.g., TEFLON®) having plural perforations therethrough, porous ceramic and a biocompatible mesh material. The lids 112 and 114 may be constructed of an inert hermetic biocompatible material, such as titanium. The jacket 109 is preferably cylindrical, although other shapes are suitable.

A barrier 110 constructed of biocompatible mesh material will inhibit adjacent tissue from squeezing through the barrier 110, but will not inhibit encapsulation tissue from growing on the sensor components unless the mesh material is extremely fine and blocks the proteins and white blood cells from passing therethrough.

Alternatively, the barrier 110 may be constructed of a biocompatible wire screening which forms a shield or cage that is fine enough to prevent adjacent tissue from squeezing into the sensor chamber 104 and interfering with light transmission. Of course, this scheme will not prevent encapsulation tissue from growing on the sensor components.

FIG. 8 shows adjacent tissue and debris molecules 116 which cannot penetrate through the barrier 110, whereas glucose molecules 118 within the interstitial fluid 102 may penetrate through the barrier 110 and enter the chamber 104. Since the interstitial fluid 102 passes freely through the barrier 110, the concentration of glucose within the sensor 100 and in the area surrounding the sensor 100 is substantially the same. In FIG. 8, the source 106 may include any of the direct light emitting sources described above, or the source 106 may be the output end of an optical fiber connected to a light emitting source. Likewise, the detector 108 may be any of the photodetector(s) described above which are compatible with the respective source, or the detector 108 may be the input end of a collection optical fiber connected to one or a plurality of photodetectors. If the source 106 and detector 108 are the optical fibers, the light emitting sources and the photodetector(s) may be remote to the jacket 109. The source 106 and the detector 108 are attached to respective ends of the jacket 109.

Regardless of whether the source 106 and detector 108 in FIG. 8 are directly coupled or coupled via an optical fiber delivery system, to minimize degradation of the source 106 and detector 108, it is necessary to provide them with respective hermetic jackets 126 and 128 and biocompatible, hermetically sealed transparent windows 130 and 132. The hermetic jackets 126 and 128 are constructed of any suitable inert, biocompatible material, such as titanium. The jackets 126 and 128 block all substances and constituents of the interstitial fluid from contacting sensor components. To further minimize growth of encapsulation tissue, a coating of hydrogel or similar material may be added to the windows 130 and 132, as well as to the jackets 126 and 128.

TEFLON® does not wet. Thus, if TEFLON® is used to construct the jacket 109, the sensor chamber 104 may be filled with alcohol or a saline solution prior to insertion of the sensor 100 into the interstitial fluid. Alternatively, the sensor chamber 104 is pressurized with the solution immediately after insertion. In either case, the solution gradually exchanges itself with the fluid outside the chamber and the inside of the chamber reaches equilibrium with respect to the outside of the chamber. An insertion spout 119 may be provided through one of the lids 112 or 114 to facilitate chamber filling.

Figure 9:
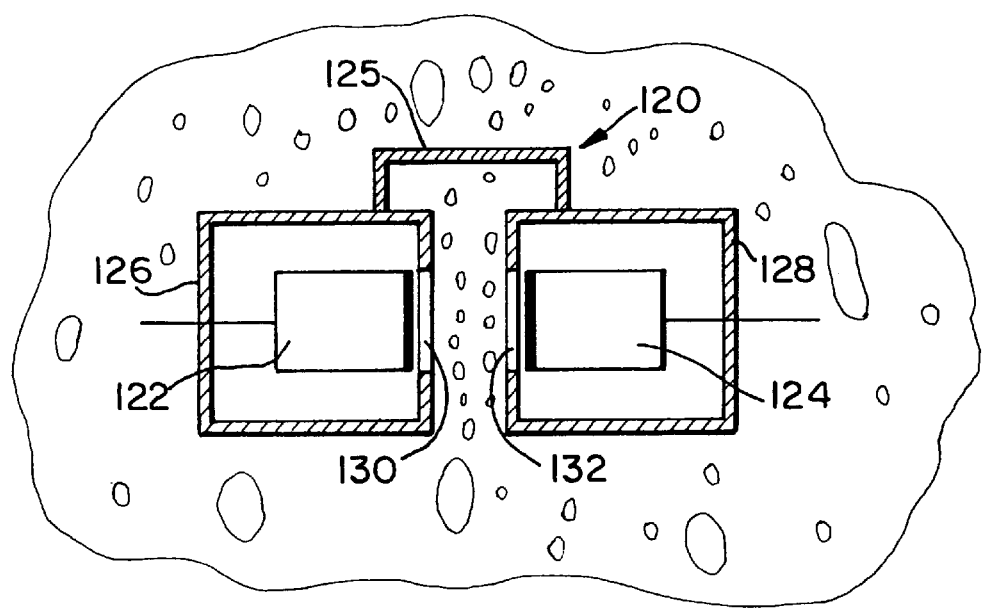

FIG. 9 shows another embodiment of an open sensor 120 suitable for use in an interstitial fluid environment. This sensor 120 includes a source 106 and a detector 108 similar to those in FIG. 8, which are protected by similar jackets 126 and 128 and optically transparent windows 130 and 132. The output of the source 122 and the input of the detector 124 are spaced from each other by a predetermined distance. A rigid coupler 125 attached to the jackets 126 and 128 maintains the predetermined distance between the source 122 and the detector 124.

In FIG. 9, the source 122 may be a direct light emitting source or a plurality of sources, as described above, and the detector 124 may be a single photodetector or a plurality of photodetectors, as also described above. Alternatively, the source 122 and detector 124 may be optical fibers connected to respective light emitting source(s) and photodetector(s), wherein the optical fibers function as a light delivery system. In the latter case, the light emitting source(s) and photodetector(s) may be remote from the open sensor 120.

Other techniques may be used in any of the embodiments shown in FIGS. 1–9 to prevent or inhibit encapsulation tissue from growing on or around sensor components. Examples of potentially suitable schemes include using heat, electric fields, or electric current, either constantly or sporadically. For example, protein becomes denatured at 60° C. Thus, a daily heat blast lasting for a few seconds may be sufficient to prevent growth. One alternative technique to a physical barrier which minimizes the problem of adjacent tissue getting in between the source and detector is to physically place the sensor in the interstitial fluid environment so that the sensing chamber is a significant distance away from the adjacent tissue.

The spectral information obtained at the output of the photodetector 44 or its equivalent is delivered to the processor 18 for spectral analysis. As discussed above, the processor 18 also receives a signal from the calibration detector 40. When measuring blood constituents using the sensor of FIG. 1, the signal received from the photodetector 44 contains spectral information from all substances which received light from the source 36. Thus, there is spectral information from the fluid of interest (e.g., blood) as well as spectral information from extraneous tissue, including the vein wall of the vein 14 and the encapsulation tissue 48. There may be additional spectral information from interstitial fluid and gel disposed between the sensor 10 and the vein 14. Hereafter, the spectral information associated with the fluid of interest is referred to as the "spectra of the fluid" or "fluid spectra", whereas the spectral information associated with extraneous tissue, including the vein wall of the vein 14 and the encapsulation tissue 48, and any solids within the interstitial gel is referred to as the "spectra of tissue" or "tissue spectra." The combination of both spectra is referred to herein as the "composite spectra." One goal of the processor 18 is to extract the fluid spectra from the composite spectra and to use the fluid spectra to obtain the concentration of the fluid constituent of interest or alternatively, to correct for the contributions of the tissue spectra to obtain accurate predictions of the constituent concentration.

Figure 10:
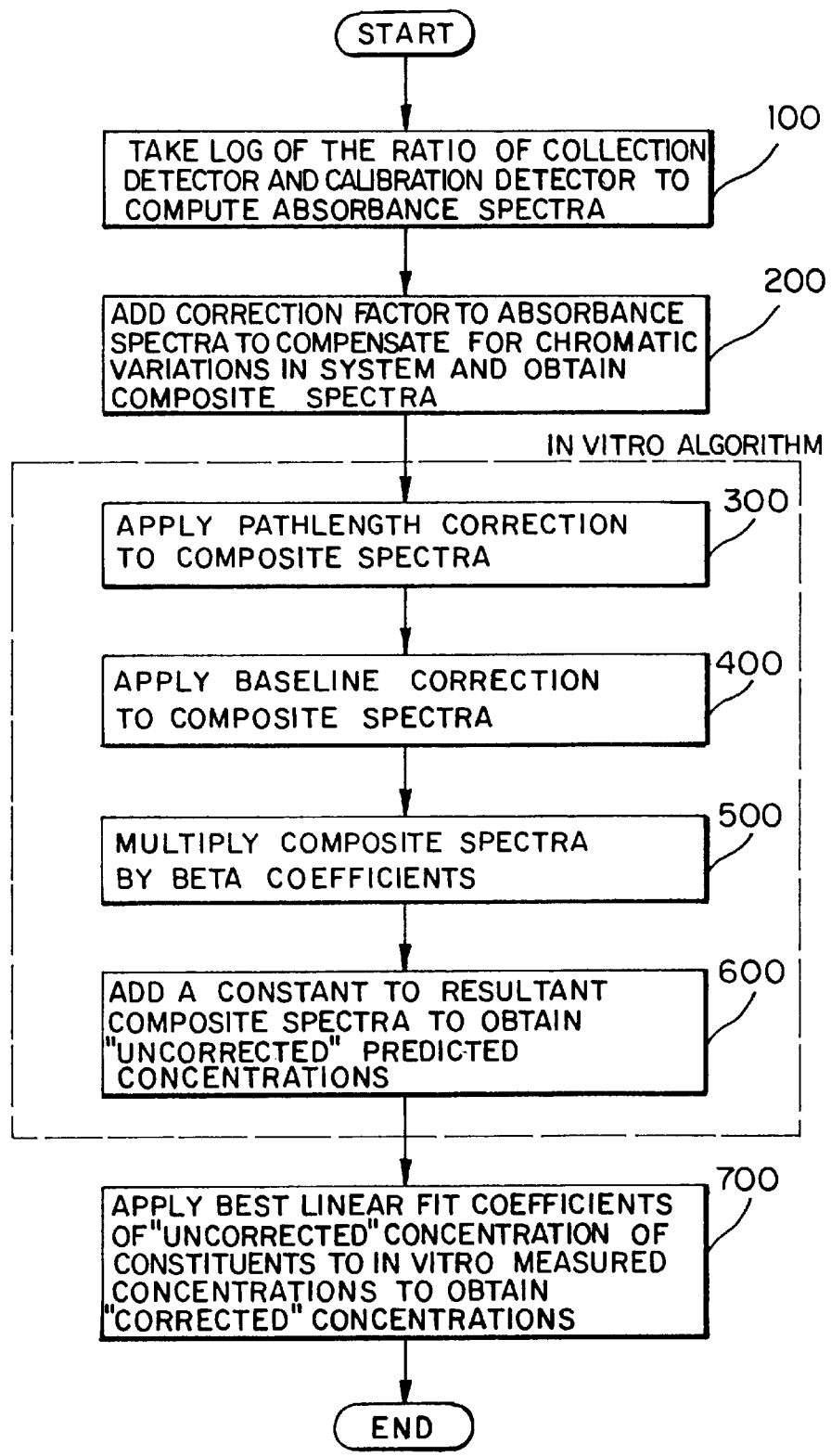
FIG. 10 is a flowchart of the steps for processing spectra obtained from an in vivo sensor of the present invention.

FIG. 10 is a flowchart of the steps performed in the processor 18 using sensor 10 of FIG. 1. Generally, the processor 18 takes spectral data output from the detector 16 and applies an in vitro algorithm to determine the fluid constituent(s) of interest. The in vitro algorithm is generated by correlating the Fourier Transform Infrared (FT-IR) spectroscopy transmission measurements of fluid samples from a statistically significant number of people to fluid samples measured using conventional techniques (i.e., techniques other than the technique of the present invention). A statistical model is applied to the FT-IR data, and the in vitro algorithm is optimized for the best least-squares prediction error and the least number of spectral points. The in vitro algorithm therefore determines the spectral points to be measured and their relative weighting of absorptivity. The algorithm is then applied to the in vivo measured spectral data to determine the concentration of selected fluid constituent(s).

Referring to FIG. 10, the processor 18 computes the absorbance spectra by taking the log of the ratio of the output of the detector 16 and the output of the calibration detector 40 for each wavelength (step 100) and adding a correction factor (step 200) to correct for (1) variability in responsivity between the detectors 16 and 40, and (2) chromatic differences in the optical systems. The resultant signal is the composite absorbance spectra or simply "composite spectra" referred to above.

Next, the processor 18 applies an in vitro algorithm, defined by steps 300–600 within dashed lines in FIG. 10, to the composite spectra. The first step in the in vitro algorithm is to apply a pathlength correction to the composite spectra (step 300). One method of performing this step is to divide the composite spectra by the difference in absorbance of the composite spectra at two wavelengths, suitably chosen for pathlength normalization. Another method is to divide the composite spectra by the "computed pathlength" as determined by a Partial Least Squares algorithm. After the pathlength correction is completed, the processor 18 applies a baseline correction to the composite spectra (step 400). One method for performing a baseline correction is by subtracting the absorbance (also pathlength corrected) at a third wavelength from the pathlength corrected composite spectra. The resulting composite spectra is now both pathlength and baseline corrected. Alternatively, the baseline correction may be applied before the pathlength correction by reversing the order of steps 300 and 400.

Next, the processor 18 computes an "uncorrected" concentration of the desired constituents by multiplying the pathlength-and-baseline-corrected composite spectra by beta coefficients (step 500) and then adding a constant to the result (step 600). The concentration is referred to as "uncorrected" because the beta coefficients are applied to the composite spectra which includes the extraneous tissue spectra, and not just the fluid spectra of interest.

DETERMINATION OF THE IN VITRO ALGORITHM

The preferred embodiment of the invention uses the Norris regression model to generate the optimum in vitro algorithm. Also, in the preferred embodiment of the invention, the choice of wavelengths and their corresponding beta coefficients are determined on an in-vitro basis, and ideally on a cross-population basis. Fluid samples representative of the fluid being measured are collected from a statistically significant group of people, such as a few hundred people. Care should be taken to avoid altering the chemistry of the fluid samples due to exposure to air, time, and the like. Ideally, the chemical constituents of both the desired constituents and other constituents which affects the spectra span essentially the entire physiological range for both healthy and sick individuals. It is also important that other physiological variables such as temperature and pH span the entire physiological range so that the calibration model holds true over a wide variation of patient health conditions.

After the fluid samples are collected, a spectra of the fluid is taken using a conventional spectrophotometry technique, such as by using a scanning or FT-IR spectrophotometer having a white light source. In addition, the concentrations of the desired constituents (e.g., glucose) are also measured by a conventional non-spectroscopic means, such as chemical assay. To allow for pathlength correction, cuvettes of several pathlengths should be used, covering the range of pathlengths ultimately being measured in vivo.

When generating the in vitro algorithm for application in steps 300, 400 and 500, the wavelengths used for pathlength correction, baseline correction and beta coefficients are preferably reiteratively optimized to provide the least-squares fit. However, before this optimization is performed, some initial guesses must be made for the wavelengths.

For the pathlength correction, which requires at least two wavelengths, the guess for the first wavelength may be obtained by computing the correlation coefficient for the spectra obtained from the in vitro samples with the measured pathlength, and choosing the coefficient which gives a correlation as close as possible to unity. The guess for the second wavelength may be obtained by computing the correlation coefficient of each wavelength of the spectra divided by the difference between the absorbance at each wavelength and the absorbance at the first wavelength with measured pathlength, and again choosing a correlation coefficient as close as possible to unity.

The actual pathlength correction involves dividing the absorbance spectra with the difference in absorbance at the first and second wavelength, as described above.

For the baseline correction, the initial guess for the offset wavelength may be empirically determined by looking at the spectra and then choosing a wavelength in a region of greatest flatness.

For the beta coefficients, the initial guesses for the wavelengths may be determined by computing the correlation of the measured constituents with the spectra and choosing wavelengths with correlation coefficients that are as close as possible to +1 or −1. It is also possible to obtain even better guesses for initial wavelengths by using wavelengths which have the largest beta coefficients (in absolute value), as determined in a Partial Least Squares (PLS) routine.

The beta coefficients are chosen by finding coefficients which provide a best least-squares fit of the spectra at the initially guessed wavelengths to the measured concentration of the constituents. Once the beta coefficients are optimized for the initial "guessed" wavelengths, the process is repeated, sequentially varying each wavelength and reoptimizing the beta coefficients to produce the best least-squares fit, thereby obtaining an optimized set of discrete wavelengths and corresponding beta coefficients. Ultimately, the standard error of calibration tends to asymptotically approach some minimum value.

The process described above provides an in vitro algorithm for calibrating the measured spectra at a finite number of wavelengths to the measured concentration (steps 300 and 400) and for computing an uncorrected concentration of desired constituents (steps 500 and 600). After these steps are performed, it is still necessary to correct for tissue spectra and obtain "corrected" concentrations.

In an implantable sensor, there is invariably extraneous tissue surrounding the fluid which contains the desired constituents and which creates the issue spectra. There are variations from person to person in both chemical composition and thickness of the encapsulation tissue, as well as in other extraneous tissue. In general, the extraneous tissue alters the spectra taken by the sensor. Unless some method is used to compensate for the extraneous tissue, it will cause an error in the computed concentrations of chemical constituents because the in vitro algorithm was developed using in vitro fluid samples (which do not have extraneous tissue). However, as long as the encapsulation tissue is stable with time, one can completely compensate for such tissue.

METHODS TO GENERATE ALGORITHM TO ACCOUNT FOR OR COMPENSATE FOR EXTRANEOUS TISSUE

In one preferred compensation method, a best linear fit on each individual patient is performed of the uncorrected concentration of the constituents (output of step 600) to the concentrations measured in vitro by conventional means, and a set of best linear fit coefficients is obtained. This measurement should be done after a period in time sufficiently long for the encapsulation tissue to reach steady-state (typically, greater than four weeks). These coefficients are stored in the processor 18 for step 700. The coefficients are applied to the uncorrected concentration of constituents to obtain predicted concentrations which are "corrected" for the extraneous tissue (step 700).

To obtain the most accurate calibration of the uncorrected concentrations to the corrected concentrations, the concentrations of the desired constituents for a particular patient should span the likely range of measurement.

For example, if the sensor is a blood glucose sensor, the calibration should be done over a range of glucose values ranging from 25 mg/dl to 300 mg/dl.

ALTERNATIVE EMBODIMENTS TO DETERMINATION OF THE IN VITRO ALGORITHM

An alternative approach to determining values for the in vitro algorithm is to apply multivariate analysis using PLS optimization to the in vitro data. The exact same in vitro data is collected (spectra, concentrations and pathlengths) on a cross-population basis as described above in the section labeled "DETERMINATION OF THE IN VITRO ALGORITHM". In one example, a PLS routine from Galactic Industries, Salem, N.H., corrects for pathlength variability by using the measured pathlength as the first constituent and the other measured constituents as second and greater constituents. Initially, the entire spectral region may be used. Next, the routine determines the standard error of prediction on a cross-calibration approach and the beta coefficients for both pathlength and for each chemical constituent.

When using this alternative approach, steps 300, 400 and 500 in FIG. 10 are modified as follows:

Step 300 (pathlength correction)—(1) determine pathlength by applying the beta coefficients for pathlength determined above to the composite spectra, and (2) divide the composite spectra by the computed pathlength.

Step 400 (baseline correction)—This step is optional and may be performed before or after step 300.

Step 500—Apply the beta coefficients as determined above in the PLS algorithm to the pathlength corrected composite spectra.

In the PLS technique, use of the entire spectral region as measured by a spectrophotometer typically does not yield the best predicted error or standard error of calibration, nor is it the most efficient method. Improvements in both accuracy and efficiency of the in vitro algorithm are possible by choosing spectral regions where the beta coefficients are the greatest and eliminating spectral regions where the beta coefficients are the smallest. This process involves reiteratively optimizing selected spectral regions and finding a limited number of spectral points which yield adequate cross-calibration and predicted error. Ideally, as few spectral points as possible should be chosen, consistent with a low cross-calibration error, to minimize the cost and complexity of the sensor. For example, each spectral point may correspond to a different diode.

Other statistical models which may alternatively be used for generating the optimum algorithm include Principal Component Regression, Neural Networks, and combinations of all of the above-described models. Second derivative data is used to minimize problems with baseline shift and spectral structure enhancement caused by scattering and pathlength variability.

ALTERNATIVE METHODS TO CORRECT FOR EXTRANEOUS TISSUE

The most obvious method to correct for extraneous tissue is to choose wavelengths for the in vitro algorithm in which the composite spectra is not particularly affected by the extraneous tissue. In many cases, this may not be possible. Hence, a correction such as step 700 in FIG. 10 must be performed.

Another possible method to correct for the extraneous tissue is to subtract a "representative spectra" of the extraneous tissue. This method involves adding an additional step between steps 200 and 300 of FIG. 10. The representative spectra of the extraneous tissue would be subtracted from the composite spectra to obtain a spectra representative of the fluid alone. The "representative spectra" (obtained as described below) would be patient specific. Steps 300 through 600 would be applied to the "fluid spectra" rather than the composite spectra in FIG. 10. Step 700 would be deleted as it would not be necessary.

The representative spectra may be obtained in several ways. One way is to take a number of in vitro fluid samples on each patient after the sensor has been implanted for a period of time sufficiently long for the encapsulation tissue to reach steady-state. Simultaneous to the in vitro fluid samples being taken, the spectra of corresponding composite spectra would be taken by the implantable sensor. The spectra on the in vitro fluid samples would be taken using either an FT-IR, scanning spectrophotometer, or dedicated spectrophotometer similar to the implanted one. It can be assumed that the representative spectra of the extraneous tissue is constant from sample to sample, for each patient. Hence, the representative spectra of the extraneous tissue can be found by finding the spectra which best fits the difference between the composite spectra and the product of a constant times the spectra of the corresponding in vitro fluid sample. The constant which is multiplied with the spectra of the in vivo fluid sample is to allow for variable in vivo fluid pathlengths, due to blood flow changes for example. The representative extraneous spectra is henceforth stored in the processor and used in the additional step.

The difficulty with this approach is that extreme care must be taken to ensure that the temperature at which the in vitro sample is taken is held to the same temperature as the corresponding in vivo sample.

A variation to the determination of the representative extraneous spectra is to take the spectra of representative constituents of the extraneous tissue such as a vein wall, collagen, and the like, and determine the best linear combination of these constituents which best fit the difference between the composite spectra and the product of a constant times the spectra of the corresponding in vitro fluid sample. Every other step is the same as outlined above.

Still another way to compensate for the contributions of tissue spectra when measuring across a pulsating blood vessel, such as an artery, is to take the composite spectra at the maximum and minimum of the pulse, and then subtract the two spectra. The subtracted spectra is essentially that of blood alone, although there is a small component due the change in thickness of the vessel wall.

PROCESSOR DETAILS

Referring to FIG. 1, the corrected concentrations of constituents may be shown on the display 20, used to trigger the alarm 22 or used to control a medication dispenser 23. The corrected concentration values, and the date and time of measurement may optionally be stored in a memory (not shown) associated with the processor 18. The processor 18 may signal to the implantable sensor 10 via telemetry to make more frequent measurements if either the trending or the measured value of the constituents are determined to be problematic. Ideally, a physician would set alarm and measurement frequency parameters.

The processor 18 also detects "outlier data," which is data that falls outside of preset bounds due to a sensor malfunction). If outlier data occurs, the processor 18 telemeters the sensor 10 to take another measurement, and triggers the alarm 22 if subsequent measurements are also outside of preset bounds.

The processor 18 may be sporadically calibrated against conventionally obtained fluid constituent measurements to prevent long-term drift. For example, when the sensor 10 is used for glucose monitoring, the processor 18 may be sporadically calibrated against blood glucose measured by chemical assay. One form of this calibration may be to supply a new set of best linear fit coefficients of step 700.

If the processor 18 is used for feedback control, the processor output signal may be used to directly control the dispenser 23, or the dispenser 23 may have its own processor (not shown) for receiving the output signal and controlling the dispensed dose.

The present invention is particularly useful for detecting glucose concentration in blood and interstitial fluid. However, the invention may also be used to measure other body fluid constituents, including proteins, cholesterol, and other blood constituents.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method of determining a concentration of a constituent of body fluid in a mammal using in vivo spectroscopy, the method comprising the step of:

(a) implanting a sensor system in the mammal by setting the sensor system in place to allow plural measurements to be taken at different time periods from a single in vivo position, the sensor system including a source of light which emits at a plurality of different wavelengths, at least one of the wavelengths being in the infrared region, and a detector for detecting light emitted from the source, the source and the detector located so that (i) the light output from the source interacts with a body fluid before being received by the detector, and (ii) light from each of the different wavelengths has a substantially collinear optical path through the fluid with respect to one another;

(b) emitting light from the source;

(c) obtaining a signal at an output of the detector which contains spectra of the body fluid at each of the different wavelengths; and (d) analyzing the signal to determine the concentration of the constituent of the body fluid.

2. A method according to claim 1 wherein step (a) includes positioning the sensor system so that the infrared light passes through body fluid containing the at least one constituent and extraneous tissue, step (c) includes obtaining composite spectra which includes spectra of the fluid and spectra of the tissue, the tissue spectra resulting from the extraneous tissue, and step (d) further includes correcting for the spectra of the tissue.

3. A method according to claim 2 wherein step (d) includes:

(i) applying a pathlength correction to the composite spectra;

(ii) applying a baseline correction to the composite spectra;

(iii) multiplying the pathlength and baseline corrected composite spectra by beta coefficients and adding a constant thereto to obtain a concentration of the at least one constituent which is uncorrected for the tissue spectra; and (iv) applying best linear fit coefficients to the uncorrected concentration of the at least one constituent of the body fluid to obtain a concentration of the at least one constituent which is corrected for the tissue spectra.

4. A method according to claim 3 further comprising, prior to performing step (d), determining the beta coefficients in vitro by the steps of:

(i) collecting in vitro fluid samples from a statistically significant plurality of mammals;

(ii) obtaining spectra of the fluid samples using a scanning or FT-IR spectrophotometer having a white light source;

(iii) correlating the spectra of the in vitro samples to the concentration of the at least one constituent measured using non-spectroscopic means; and (iv) selecting a finite number of discrete wavelengths and respective beta coefficients which provide a best least-squares fit of the spectra of the in vitro samples to the measured concentration of the at least one constituent.

5. A method according to claim 4 wherein the step of selecting the beta coefficients and the respective discrete wavelengths further includes the steps of:

(v) initially guessing for the discrete wavelengths by either selecting wavelengths with correlation coefficients in step (iii) that are as close as possible to +1 or −1 or by selecting wavelengths which have the largest beta coefficients in absolute value as determined in a Partial Least Squares routine;

(vi) optimizing the beta coefficients for the initial guessed wavelengths; and (vii) sequentially varying each wavelength and reiteratively optimizing the beta coefficients to produce the least-squares fit, thereby obtaining an optimized set of discrete wavelengths and beta coefficients.

6. A method according to claim 2 wherein step (d) includes:

(i) subtracting a representative spectra of extraneous tissue from the composite spectra to obtain the fluid spectra;

(ii) applying a pathlength correction to the fluid spectra;

(ii) applying a baseline correction to the fluid spectra; and (iii) multiplying the pathlength and baseline corrected fluid spectra by beta coefficients and adding a constant thereto to obtain a concentration of the at least one constituent.

7. A method according to claim 1 wherein step (b) includes emitting light at the different wavelengths at a substantially single period of time.

8. A method according to claim 7 wherein the substantially single period of time is less than about 100 microseconds.

9. A method according to claim 1 wherein the body fluid is blood, and step (a) includes positioning the implantable sensor system extravascularly, the source and the detector being arranged so that the light output from the source interacts with a blood vessel before being received by the detector, and step (d) includes analyzing the signal to determine the concentration of at least one blood constituent.

10. A method according to claim 9 wherein step (d) includes analyzing the signal to determine the concentration of blood glucose.

11. A method according to claim 1 wherein the body fluid is blood, and step (a) includes positioning the implantable sensor system around a vascular membrane, the source and the detector being arranged so that the light output from the source interacts with the vascular membrane before being received by the detector, and step (d) includes analyzing the signal to determine the concentration of at least one blood constituent in the vascular membrane.

12. A method according to claim 11 wherein step (d) includes analyzing the signal to determine the concentration of blood glucose.

13. A method according to claim 1 wherein the body fluid is interstitial fluid or gel, and step (a) includes positioning the implantable sensor system in a region of the body containing interstitial fluid or gel, the source and the detector being arranged so that the light output from the source interacts with the interstitial fluid or gel before being received by the detector, and step (d) includes analyzing the signal to determine the concentration of at least one constituent of the interstitial fluid or gel.

14. A method according to claim 13 wherein step (d) includes analyzing the signal to determine the concentration of glucose in the interstitial fluid or gel.

15. A method according to claim 1 wherein in step (b), the light emitted from the source has wavelengths in the near-infrared region.

16. A method according to claim 15 wherein all of the emitted wavelengths are in the near-infrared region.

17. A method according to claim 1 wherein step (b) includes sequentially emitting light at the different wavelengths from the source in a pulsed manner, light from all of the wavelengths being emitted within a substantially single period of time.

18. A method according to claim 1 wherein the detector of the sensor system is arranged to receive light transmitted through the body fluid, and the signal obtained in step (c) includes the transmitted light.

19. A method according to claim 1 wherein the detector of the sensor system is arranged to receive light reflected or scattered by the body fluid, and the signal obtained in step (c) includes the reflected or scattered light.

20. A method according to claim 1 wherein the source has a plurality of individual source elements, each source element emitting a different wavelength, and step (b) includes emitting the light from the plurality of individual source elements.

21. A method according to claim 1 further comprising the step of:

(e) measuring the output power of the source, wherein step (d) includes the step of obtaining an absorbance spectra by taking a log of the ratio of the detector output signal of step (c) and the output power of the source for each of the different wavelengths.

22. A method according to claim 1 wherein the source of light emits at at least three different wavelengths, and step (b) includes emitting the light from the source at at least the three different wavelengths.

23. An implantable sensor adapted for determining a concentration of a chemical constituent of body fluid in a mammal using in vivo spectroscopy, the sensor comprising:

(a) a source of light which emits at a plurality of different wavelengths, at least one of the wavelengths being in the infrared region;

(b) a detector for detecting light emitted from the source and outputting a signal which contains spectra of the body fluid at each of the different wavelengths, wherein the source and the detector are adapted to be located so that (i) the light output from the source interacts with a body fluid before being received by the detector, and (ii) light from each of the different wavelengths has a substantially collinear optical path through the fluid with respect to one another, the source and detector adapted to be fully implanted and set in place to allow plural measurements to be taken at different time periods from a single in vivo position; and (c) a processor for analyzing the signal and the spectra, and determining therefrom the concentration of the chemical constituent in the body fluid.

24. A sensor according to claim 23 further comprising:

(d) a controller for causing the source to emit light at the different wavelengths within a substantially single period of time.

25. A sensor according to claim 24, wherein the substantially single period of time is less than about 100 microseconds.

26. A sensor according to claim 23, wherein the source includes a plurality of individual source elements, each source element emitting light at a different wavelength in the infrared region.

27. A sensor according to claim 26, wherein the individual source elements include laser diodes.

28. A sensor according to claim 27, wherein the individual source elements include light emitting diodes.

29. A sensor according to claim 23, wherein the source includes:

(i) a plurality of individual source elements each emitting light at one of the different wavelength in the infrared region; and (ii) single core multimode optical fiber for receiving the light at the emitted wavelengths, the output of the optical fiber being the emitted output of the source, wherein the optical fiber has a length sufficient to allow for substantial wavelength mixing as light at the emitted wavelengths travels through the optical fiber towards an output end of the optical fiber, the wavelength mixing creating the substantially collinear optical path through the fluid for the different wavelengths with respect to one another.

30. A sensor according to claim 29, wherein the length of the optical fiber is greater than 1 meter.

31. A sensor according to claim 23, wherein the source includes:

(i) a plurality of individual source elements, each emitting light at one of the different wavelength in the infrared region; and (ii) a diffraction grating coupler for receiving the light at the emitted wavelengths and outputting the light at the different wavelengths in a substantially collinear optical path with respect to one another, the output of the diffraction grating coupler being the emitted output of the source.

32. A sensor according to claim 23, wherein the source includes a tunable laser for emitting light at the different wavelengths, the tunable laser being programmed to scan through the different wavelengths.

33. A sensor according to claim 23, wherein the source includes:

(i) a broadband light which simultaneously emits light which includes at least the different wavelengths; and (ii) a tunable spectral filter disposed between the output of the broadband light and the output of the source, the tunable spectral filter being programmed to scan through the different wavelengths.

34. A sensor according to claim 23, wherein the source includes a broadband light source which simultaneously emits light having a spectra that includes at least the different wavelengths, and the detector includes:

(i) a single collection optical fiber for receiving broadband light which has interacted with the body fluid;

(ii) a fixed grating for receiving the broadband light which has interacted with the body fluid and spectrally separating the received broadband light into a plurality of predefined wavelengths; and (iii) a plurality of photodetectors, wherein each photodetector detects light at one of the predefined wavelengths.

35. A sensor according to claim 23, wherein light at the different wavelengths is output in a time-sequenced manner, and the detector includes a single photodetector which processes the light at the different wavelengths in coordination with the time-sequencing.

36. A sensor according to claim 23, wherein the source emits light at wavelengths in the near-infrared region from about 1,000 nanometers to about 2,500 nanometers.

37. A sensor according to claim 23, wherein the detector of the sensor system is arranged to receive light transmitted through the fluid, and the signal analyzed by the processor includes the directly transmitted light.

38. A sensor according to claim 23, wherein the detector of the sensor system is arranged to receive light reflected or scattered by the fluid, and the signal analyzed by the processor includes the reflected or scattered light.

39. A sensor according to claim 23, wherein the detector includes a photodetector.

40. A sensor according to claim 23, wherein the source includes a plurality of individual source elements arranged in close proximity to each other relative to the distance between the individual elements and the detector, so that the plurality of source elements define the substantially collinear optical path.

41. A sensor according to claim 23, wherein the sensor includes a plurality of individual source elements, each individual source element being frequency modulated at a unique predetermined frequency.

42. A sensor according to claim 23, wherein the sensor includes a calibration detector for detecting the output power of the source, the detected output power being communicated to the processor for use in the signal analysis.

43. A sensor according to claim 23, wherein the processor includes an output signal for indicating that the concentration of the at least one chemical constituent is outside of a predetermined range.

44. A sensor according to claim 23, wherein the source of the light emits at at least three different wavelengths.

45. An infusion pump system for monitoring at least one chemical constituent of body fluid in a mammal and delivering medication to the mammal, the system comprising:

(a) an implantable sensor adapted for determining a concentration of a chemical constituent of body fluid in a mammal using in vivo spectroscopy, the sensor including:

(i) a source of light which emits at a plurality of different wavelengths, at least one of the wavelengths being in the infrared region;

(ii) a detector for detecting light emitted from the source and outputting a signal which contains spectra of the body fluid at each of the plurality of different wavelengths, wherein the source and the detector are adapted to be located so that (1) the light output from the source interacts with a body fluid before being received by the detector, and (2) light from each of the plurality of different wavelengths has a substantially collinear optical path through the fluid with respect to one another; and (iii) a processor for analyzing the signal and the spectra, and determining therefrom the concentration of the chemical constituent of the body fluid; and (b) a pump module connected to the sensor for dispensing doses of medicine in response to the concentration of the chemical constituent output from the processor.

46. A system according to claim 45, wherein the sensor further comprises:

(iv) a controller for causing the source to emit the light at the plurality of different wavelengths within a substantially single period of time.

47. A system according to claim 45, wherein the sensor determines the concentration of blood glucose in a body fluid of the mammal, and the medication dispenser is an insulin infusion pump for dispensing doses of insulin.

48. An implantable sensor adapted for determining a concentration of a chemical constituent of body fluid in a mammal using in vivo spectroscopy, the sensor comprising:

(a) a chamber which has a porosity sufficient to allow interstitial fluid or gel to pass therethrough but which inhibits adjacent tissue and solid material from passing therethrough;

(b) a source of light disposed within the chamber that emits at a plurality of different wavelengths, at least one of the wavelengths being in the infrared region;

(c) a detector disposed within the chamber and spaced from the source for detecting light emitted from the source and outputting a signal which contains spectra of the interstitial fluid or gel at each of the plurality of different wavelengths, wherein the source and the detector are adapted to be located so that (i) the light output from the source interacts with the interstitial fluid or gel before being received by the detector, and (ii) light from each of the plurality of different wavelengths has a substantially collinear optical path through the interstitial fluid or gel with respect to one another; and (d) a processor for analyzing the signal and the spectra, and determining therefrom the concentration of the chemical constituent in the interstitial fluid or gel.

49. A method of determining a concentration of a constituent of body fluid in a mammal using in vivo spectroscopy, the method comprising the steps of:

(a) implanting a sensor system in the mammal, the sensor system including a source of light which emits at a plurality of different wavelengths, at least one of the wavelengths being in the infrared region, and a detector for detecting light emitted from the source, the source and the detector located so that (i) the light output from the source interacts with a body fluid containing the at least one constituent before being received by the detector, and (ii) light from each of the different wavelengths has a substantially collinear optical path through the fluid with respect to one another, the sensor system being positioned so that the infrared light also passes through extraneous tissue;

(b) emitting light from the source;

(c) obtaining a signal at an output of the detector which contains a composite spectra including spectra of the body fluid at each of the different wavelengths, and spectra of the tissue at each of the different wavelengths, the tissue spectra resulting from the extraneous tissue; and (d) analyzing the signal to determine the concentration of the constituent of the body fluid, the analysis including correcting for the spectra of the tissue.

50. A method according to claim 49, wherein step (d) includes:

(i) applying a pathlength correction to the composite spectra;

(ii) applying a baseline correction to the composite spectra;

(iii) multiplying the pathlength and baseline corrected composite spectra by beta coefficients and adding a constant thereto to obtain a concentration of the at least one constituent which is uncorrected for the tissue spectra; and (iv) applying best linear fit coefficients to the uncorrected concentration of the at least one constituent of the body fluid to obtain a concentration of the at least one constituent which is corrected for the tissue spectra.

51. A method according to claim 50 further comprising, prior to performing step (d), determining the beta coefficients in vitro by the steps of:

(i) collecting in vitro fluid samples from a statistically significant plurality of mammals;

(ii) obtaining spectra of the fluid samples using a scanning or FT-IR spectrophotometer having a white light source;

(iii) correlating the spectra of the in vitro samples to the concentration of the at least one constituent measured using non-spectroscopic means; and (iv) selecting a finite number of discrete wavelengths and respective beta coefficients which provide a best least-squares fit of the spectra of the in vitro samples to the measured concentration of the at least one constituent.

52. A method according to claim 51, wherein the step of selecting the beta coefficients and the respective discrete wavelengths further includes the steps of:

(v) initially guessing for the discrete wavelengths by either selecting wavelengths with correlation coefficients in step (iii) that are as close as possible to +1 or −1 or by selecting wavelengths which have the largest beta coefficients in absolute value as determined in a Partial Least Squares routine;

(vi) optimizing the beta coefficients for the initial guessed wavelengths; and (vii) sequentially varying each wavelength and reiteratively optimizing the beta coefficients to produce the least-squares fit, thereby obtaining an optimized set of discrete wavelengths and beta coefficients.

53. A method according to claim 49, wherein step (d) includes:

(i) subtracting a representative spectra of extraneous tissue from the composite spectra to obtain the fluid spectra;

(ii) applying a pathlength correction to the fluid spectra;

(iii) applying a baseline correction to the fluid spectra; and (iv) multiplying the pathlength and baseline corrected fluid spectra by beta coefficients and adding a constant thereto to obtain a concentration of the at least one constituent.

54. A method of determining a concentration of blood glucose in a mammal using in vivo spectroscopy, the method comprising the steps of:

(a) implanting a sensor system in the mammal, the sensor system being positioned extravascularly, the sensor system including a source of light which emits at a plurality of different wavelengths, at least one of the wavelengths being in the infrared region, and a detector for detecting light emitted from the source, the source and the detector located so that (i) the light output from the source interacts with blood in a blood vessel before being received by the detector, and (ii) light from each of the different wavelengths has a substantially collinear optical path through the blood vessel with respect to one another;

(b) emitting light from the source;

(c) obtaining a signal at an output of the detector which contains spectra of the blood at each of the different wavelengths; and (d) analyzing the signal to determine the concentration of glucose in the blood.

55. A method of determining a concentration of blood glucose in a mammal using in vivo spectroscopy, the method comprising the steps of:

(a) implanting a sensor system in the mammal, the sensor system being positioned around a vascular membrane, the sensor system including a source of light which emits at a plurality of different wavelengths, at least one of the wavelengths being in the infrared region, and a detector for detecting light emitted from the source, the source and the detector located so that (i) the light output from the source interacts with blood in the vascular membrane before being received by the detector, and (ii) light from each of the different wavelengths has a substantially collinear optical path through the vascular membrane with respect to one another;

(b) emitting light from the source;

(c) obtaining a signal at an output of the detector which contains spectra of the blood at each of the different wavelengths; and (d) analyzing the signal to determine the concentration of glucose in the vascular membrane.

56. A method of determining a concentration of a constituent of interstitial fluid or gel in a mammal using in vivo spectroscopy, the method comprising the steps of:

(a) implanting a sensor system in the mammal in a region of the body containing interstitial fluid or gel, the sensor system including a source of light which emits at a plurality of different wavelengths, at least one of the wavelengths being in the infrared region, and a detector for detecting light emitted from the source, the source and the detector located so that (i) the light output from the source interacts with the interstitial fluid or gel before being received by the detector, and (ii) light from each of the different wavelengths has a substantially collinear optical path through the interstitial fluid or gel with respect to one another;

(b) emitting light from the source;

(c) obtaining a signal at an output of the detector which contains spectra of the interstitial fluid or gel at each of the different wavelengths; and (d) analyzing the signal to determine the concentration of at least one constituent of the interstitial fluid or gel.

57. A method according to claim 56, wherein step (d) includes analyzing the signal to determine the concentration of glucose in the interstitial fluid or gel.

58. A method of determining a concentration of a constituent of body fluid in a mammal using in vivo spectroscopy, the method comprising the steps of:

(a) implanting a sensor system in the mammal, the sensor system including a source of light which emits at a plurality of different wavelengths in the near-infrared region from about 1,000 nanometers to about 2,500 nanometers, and a detector for detecting light emitted from the source, the source and the detector located so that (i) the light output from the source interacts with a body fluid before being received by the detector, and (ii) light from each of the different wavelengths has a substantially collinear optical path through the fluid with respect to one another;

(b) emitting light from the source in the near-infrared region from about 1,000 nanometers to about 2,500 nanometers;

(c) obtaining a signal at an output of the detector which contains spectra of the body fluid at each of the different wavelengths; and (d) analyzing the signal to determine the concentration of the constituent of the body fluid.

59. An implantable sensor adapted for determining a concentration of a chemical constituent of body fluid in a mammal using in vivo spectroscopy, the sensor comprising:

(a) a source of light which emits at a plurality of different wavelengths, the source including:
  (i) a plurality of individual source elements, each emitting light at a different wavelength in the infrared region, and
  (ii) a diffraction grating coupler for receiving the light at the emitted wavelengths and outputting the light at the different wavelengths in a substantially collinear optical path with respect to one another, the output of the diffraction grating coupler being the emitted output of the source;

(b) a detector for detecting light emitted from the source and outputting a signal which contains spectra of the body fluid at each of the different wavelengths, wherein the source and the detector are adapted to be located so that (i) the light output from the source interacts with a body fluid before being received by the detector, and (ii) light from each of the different wavelengths has a substantially collinear optical path through the fluid with respect to one another; and (c) a processor for analyzing the signal and the spectra, and determining therefrom the concentration of the chemical constituent in the body fluid.

60. An implantable sensor adapted for determining a concentration of a chemical constituent of body fluid in a mammal using in vivo spectroscopy, the sensor comprising:

(a) a source of light which emits at plurality of different wavelengths, at least one of the wavelengths being in the infrared region, the source including a broadband light source which simultaneously emits light having a spectra that includes at least the different wavelengths;

(b) a detector for detecting light emitted from the source and outputting a signal which contains spectra of the body fluid at each of the different wavelengths, the detector including:
  (i) a single collection optical fiber for receiving broadband light which has interacted with the body fluid;
  (ii) a fixed grating for receiving the broadband light which has interacted with the body fluid and spectrally separating the received broadband light into a plurality of predefined wavelengths; and
  (iii) a plurality of photodetectors, wherein each photodetector detects light at one of the predefined wavelengths, wherein the source and the detector are adapted to be located so that (i) the light output from the source interacts with a body fluid before being received by the detector, and (ii) light from each of the different wavelengths has a substantially collinear optical path through the fluid with respect to one another; and (c) a processor for analyzing the signal and the spectra, and determining therefrom the concentration of the chemical constituent in the body fluid.

61. An implantable sensor adapted for determining a concentration of a chemical constituent of body fluid in a mammal using in vivo spectroscopy, the sensor comprising:

(a) a source of light which emits at plurality of different wavelengths in the near-infrared region from about 1,000 nanometers to about 2,500 nanometers;

(b) a detector for detecting light emitted from the source and outputting a signal which contains spectra of the body fluid at each of the different wavelengths, wherein the source and the detector are adapted to be located so that (i) the light output from the source interacts with a body fluid before being received by the detector, and (ii) light from each of the different wavelengths has a substantially collinear optical path through the fluid with respect to one another; and (c) a processor for analyzing the signal and the spectra, and determining therefrom the concentration of the chemical constituent in the body fluid.

62. An implantable sensor adapted for determining a concentration of blood glucose in a mammal using in vivo spectroscopy, the sensor comprising:

(a) a source of light which emits at plurality of different wavelengths, at least one of the wavelengths being in the infrared region;

(b) a detector for detecting light emitted from the source and outputting a signal which contains spectra of the body fluid at each of the different wavelengths, wherein the source and the detector are adapted to be located so that (i) the light output from the source interacts with blood in a blood vessel before being received by the detector, and (ii) light from each of the different wavelengths has a substantially collinear optical path through the blood vessel with respect to one another; and (c) a processor for analyzing the signal and the spectra, and determining therefrom the concentration of glucose in the blood.

63. An implantable sensor adapted for determining a concentration of blood glucose in a mammal using in vivo spectroscopy, the sensor comprising:

(a) a source of light which emits at plurality of different wavelengths, at least one of the wavelengths being in the infrared region;

(b) a detector for detecting light emitted from the source and outputting a signal which contains spectra of the blood at each of the different wavelengths, wherein the source and the detector are adapted to be located so that (i) the light output from the source interacts with blood in a vascular membrane before being received by the detector, and (ii) light from each of the different wavelengths has a substantially collinear optical path through the vascular membrane with respect to one another; and (c) a processor for analyzing the signal and the spectra, and determining therefrom the concentration of glucose in the blood.

64. An implantable sensor adapted for determining a concentration of a chemical constituent of interstitial fluid or gel in a mammal using in vivo spectroscopy, the sensor comprising:

(a) a source of light which emits at plurality of different wavelengths, at least one of the wavelengths being in the infrared region;

(b) a detector for detecting light emitted from the source and outputting a signal which contains spectra of the interstitial fluid or gel at each of the different wavelengths, wherein the source and the detector are adapted to be located so that (i) the light output from the source interacts with the interstitial fluid or gel before being received by the detector, and (ii) light from each of the different wavelengths has a substantially collinear optical path through the interstitial fluid or gel with respect to one another; and (c) a processor for analyzing the signal and the spectra, and determining therefrom the concentration of the chemical constituent in the interstitial fluid or gel.

65. An implantable sensor according to claim 64, wherein the processor is adapted to analyze the signal to determine the concentration of glucose in the interstitial fluid or gel.

66. A method of determining a concentration of a constituent of body fluid in a mammal using in vivo spectroscopy, the method comprising the steps of:

(a) implanting a sensor system in the mammal, the sensor system including a source of light which emits at at least three different wavelengths, at least one of the wavelengths being in the infrared region, and a detector for detecting light emitted from the source, the source and the detector located so that (i) the light output from the source interacts with a body fluid before being received by the detector, and (ii) light from each of the different wavelengths has a substantially collinear optical path through the fluid with respect to one another;

(b) emitting light from the source at at least the three different wavelengths;

(c) obtaining a signal at an output of the detector which contains spectra of the body fluid at each of the different wavelengths; and (d) analyzing the signal to determine the concentration of the constituent of the body fluid.

67. An implantable sensor adapted for determining a concentration of a chemical constituent of body fluid in a mammal using in vivo spectroscopy, the sensor comprising:

(a) a source of light which emits at at least three different wavelengths, at least one of the wavelengths being in the infrared region;

(b) a detector for detecting light emitted from the source and outputting a signal which contains spectra of the body fluid at each of the different wavelengths, wherein the source and the detector are adapted to be located so that (i) the light output from the source interacts with a body fluid before being received by the detector, and (ii) light from each of the different wavelengths has a substantially collinear optical path through the fluid with respect to one another; and (c) a processor for analyzing the signal and the spectra, and determining therefrom the concentration of the chemical constituent in the body fluid.

* * * * *